(12) United States Patent
Androsov et al.

(10) Patent No.: US 10,053,424 B2
(45) Date of Patent: Aug. 21, 2018

(54) MONOMER AND POLYMER AND COMPENSATION FILM AND OPTICAL FILM AND DISPLAY DEVICE

(71) Applicant: SAMSUNG ELECTRONICS CO., LTD., Suwon-si, Gyeonggi-do (KR)

(72) Inventors: Dmitry Androsov, Suwon-si (KR); Changki Kim, Suwon-si (KR); Masashi Tsuji, Hwaseong-si (KR); Hyunseok Choi, Anyang-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 22 days.

(21) Appl. No.: 15/190,863

(22) Filed: Jun. 23, 2016

(65) Prior Publication Data

US 2017/0210709 A1    Jul. 27, 2017

(30) Foreign Application Priority Data

Jan. 27, 2016    (KR) .................. 10-2016-0010201

(51) Int. Cl.
*C07C 69/82* (2006.01)
*C07D 209/50* (2006.01)
(Continued)

(52) U.S. Cl.
CPC ............ *C07D 209/50* (2013.01); *B32B 27/06* (2013.01); *C08G 64/12* (2013.01); *C09D 169/00* (2013.01);
(Continued)

(58) Field of Classification Search
CPC .... C07D 209/50; C08G 64/12; C09D 169/00; G02B 5/3033; G02B 5/3083;
(Continued)

(56) References Cited

U.S. PATENT DOCUMENTS

| | | |
|---|---|---|
| 2001/0009293 A1 | 7/2001 | Carter et al. |
| 2009/0251650 A1 | 10/2009 | Fukagawa et al. |
| 2012/0205583 A1 | 8/2012 | Montenegro et al. |

FOREIGN PATENT DOCUMENTS

| | | |
|---|---|---|
| JP | 2003-057441 A | 2/2003 |
| JP | 2003-238685 A | 8/2003 |

(Continued)

OTHER PUBLICATIONS

STIC Search Report dated Nov. 15, 2017.*

*Primary Examiner* — Eisa B Elhilo
(74) *Attorney, Agent, or Firm* — Cantor Colburn LLP

(57) ABSTRACT

A monomer represented by Chemical Formula 1:

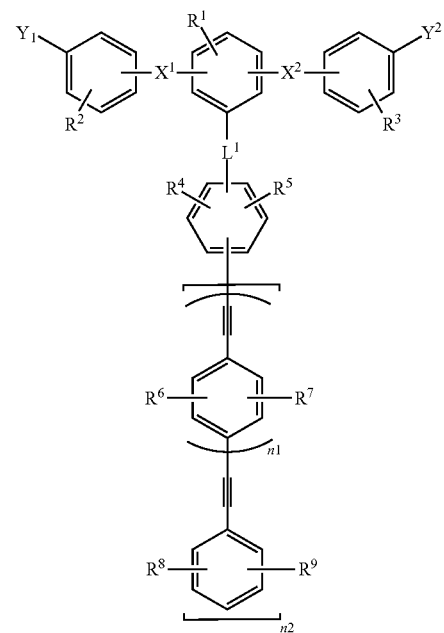

Chemical Formula 1 wherein in Chemical Formula 1, $X^1$, $X^2$, $L^1$, $Y^1$, $Y^2$, $R^1$ to $R^9$, n1, and n2 are the same as described in the detailed description.

20 Claims, 5 Drawing Sheets

(51) Int. Cl.
  *C08G 64/12* (2006.01)
  *C09D 169/00* (2006.01)
  *G02B 5/30* (2006.01)
  *G02F 1/13363* (2006.01)
  *H01L 51/52* (2006.01)
  *B32B 27/06* (2006.01)

(52) U.S. Cl.
  CPC ......... *G02B 5/3033* (2013.01); *G02B 5/3083* (2013.01); *G02F 1/13363* (2013.01); *H01L 51/5281* (2013.01); *B32B 2307/412* (2013.01); *B32B 2307/42* (2013.01); *B32B 2551/00* (2013.01)

(58) Field of Classification Search
  CPC . G02F 1/13363; H01L 51/5281; B32B 27/06; B32B 2307/412; B32B 2551/00
  See application file for complete search history.

(56) References Cited

FOREIGN PATENT DOCUMENTS

| | | | | |
|---|---|---|---|---|
| JP | 2007-086748 | A | 4/2007 | |
| KR | 2006-0090172 | A | 8/2006 | |
| KR | 2011-0041441 | A | 4/2011 | |
| KR | 2012-0100943 | A | 9/2012 | |
| WO | WO 2010/072760 | A1 * | 7/2010 | ............. C08G 65/00 |

* cited by examiner

MONOMER AND POLYMER AND COMPENSATION FILM AND OPTICAL FILM AND DISPLAY DEVICE

CROSS-REFERENCE TO RELATED APPLICATION

This application claims priority to Korean Patent Application No. 10-2016-0010201 filed in the Korean Intellectual Property Office on Jan. 27, 2016, and all the benefits accruing therefrom under 35 U.S.C. § 119, the content of which is incorporated herein in its entirety by reference.

BACKGROUND

1. Field

A monomer, a polymer, a compensation film, an optical film, and a display device are disclosed.

2. Description of the Related Art

A flat panel display may be classified into a light-emitting display device emitting light by itself and a non-emissive display device requiring a separate light source, wherein a compensation film is employed for improving the image quality thereof. However, there still remains a need in novel polymers, which can improve the properties of the existing compensation and optical films.

SUMMARY

An embodiment provides a novel monomer that is applicable to a compensation film.

Another embodiment provides a polymer obtained by polymerization of the novel monomer.

Yet another embodiment provides a compensation film including the polymer.

Still another embodiment provides an optical film including the compensation film.

Further another embodiment provides a display device including the compensation film or the optical film.

According to an embodiment, a monomer is represented by Chemical Formula 1.

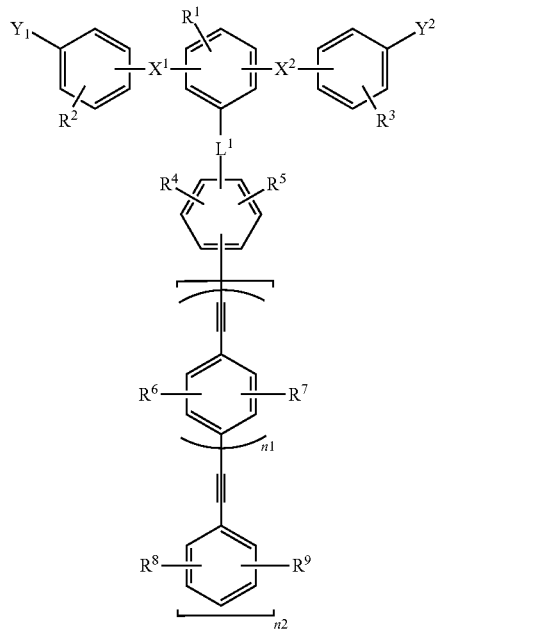

Chemical Formula 1

In Chemical Formula 1, $X^1$, $X^2$, and $L^1$ are each independently O, C(=O), C(=O)O, or C(=O)NR$^a$, $Y^1$ and $Y^2$ are each independently OH or NH$_2$, $R^1$ to $R^9$, and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, and n2 is 1 or 2.

The monomer may be represented by any one of Chemical Formulae 2 to 4.

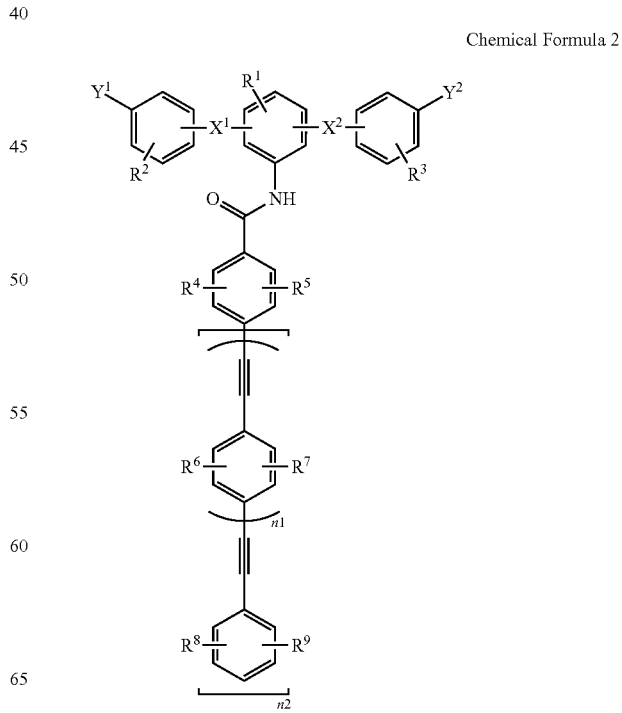

Chemical Formula 2

Chemical Formula 3

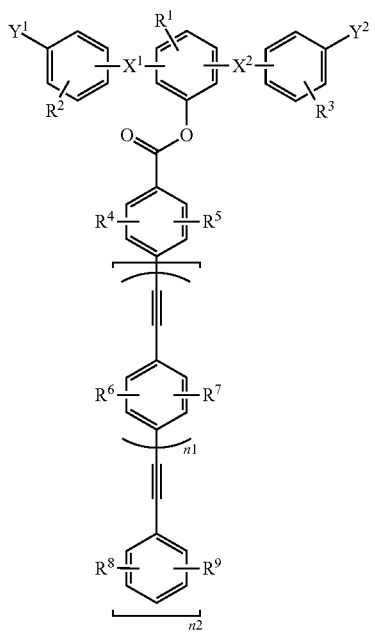

Chemical Formula 4

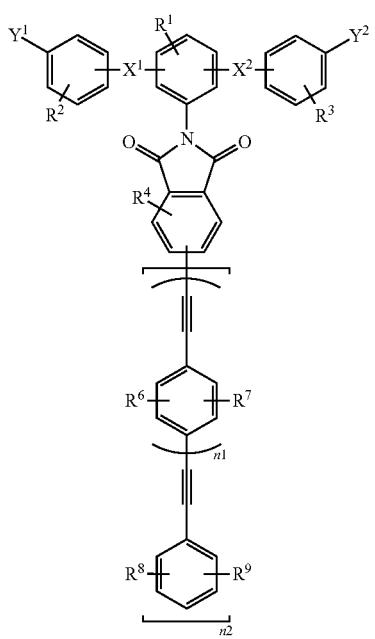

In Chemical Formulae 2 to 4, $X^1$ and $X^2$ are each independently O, C(=O), C(=O)O, or C(=O)$NR^a$, $Y^1$ and $Y^2$ are each independently OH or $NH_2$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, n1 is an integer ranging from 0 to 3, and n2 is 1 or 2.

The monomer represented by Chemical Formula 2 may be represented by any one of Chemical Formulae 2a to 2d.

Chemical Formula 2a

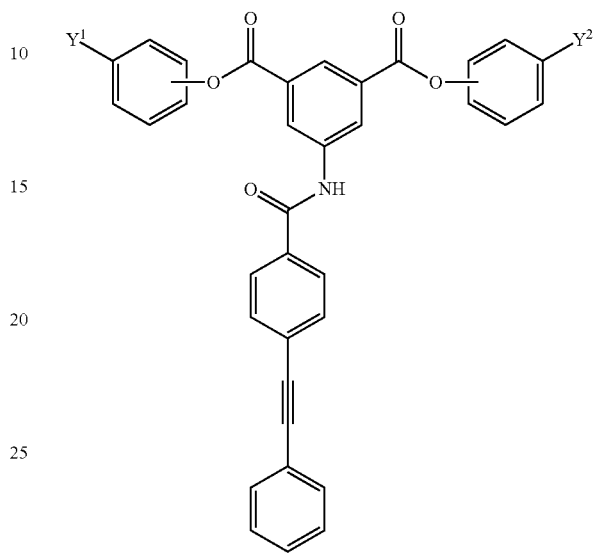

Chemical Formula 2b

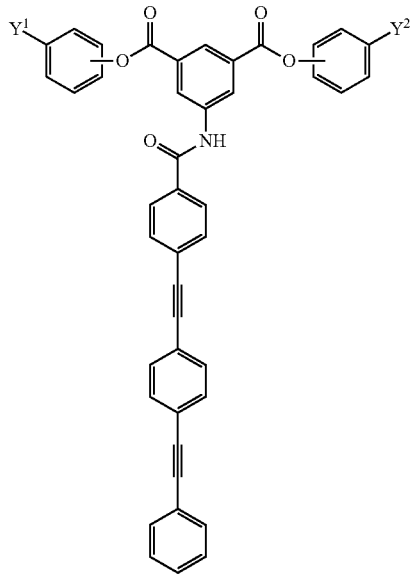

Chemical Formula 2c
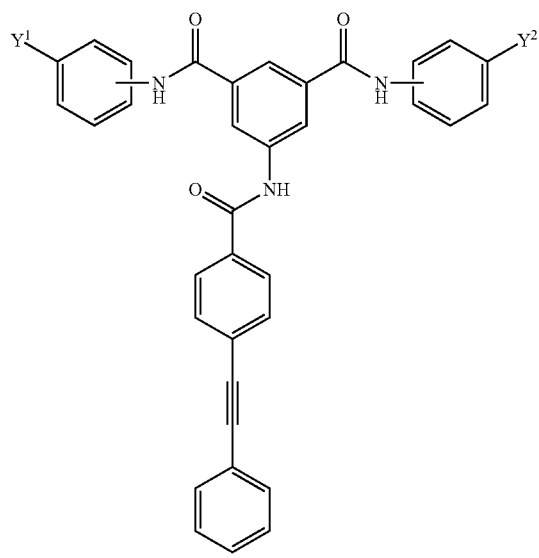
Chemical Formula 3a
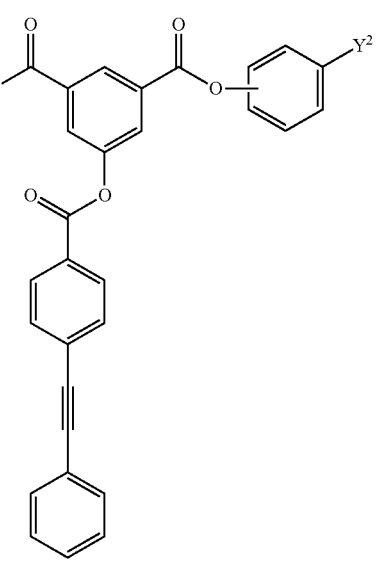
Chemical Formula 2d
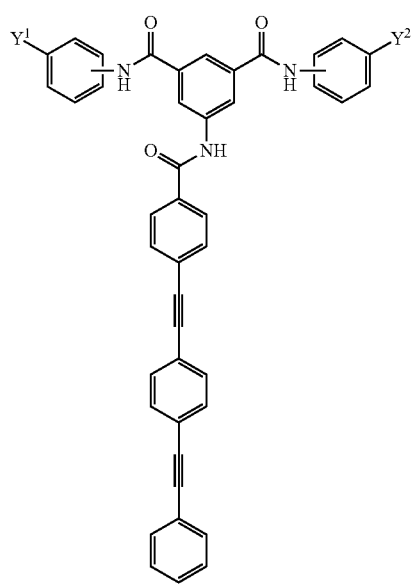
Chemical Formula 3b
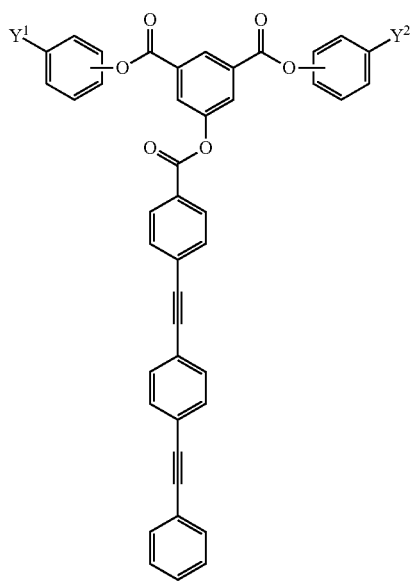
In Chemical Formulae 2a to 2d,
$Y^1$ and $Y^2$ are each independently OH or $NH_2$.
The monomer represented by Chemical Formula 3 may be represented by any one of Chemical Formulae 3a to 3d.

Chemical Formula 3c
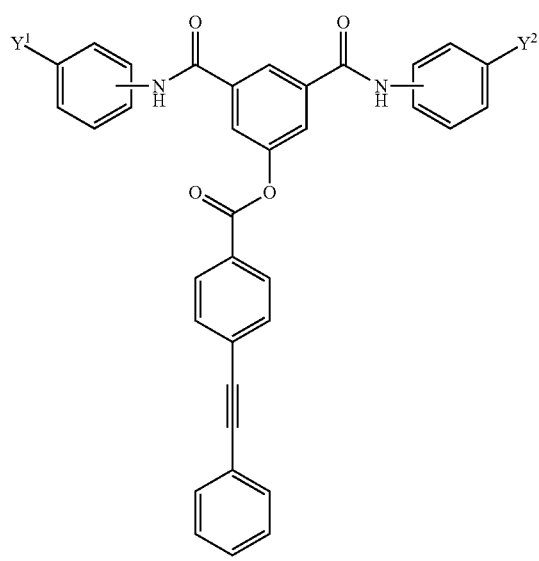
Chemical Formula 4a
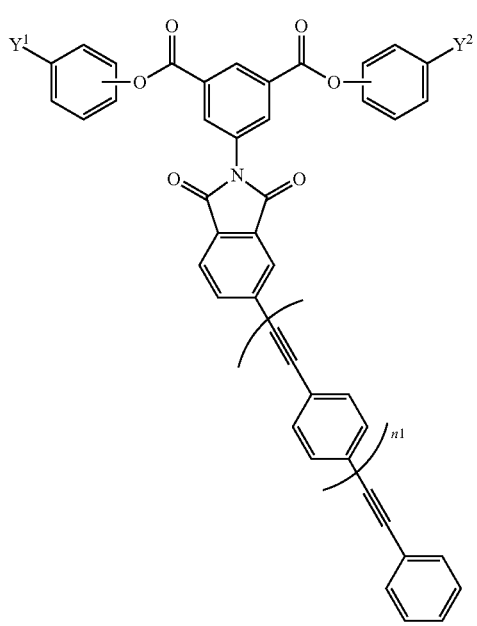
Chemical Formula 3d
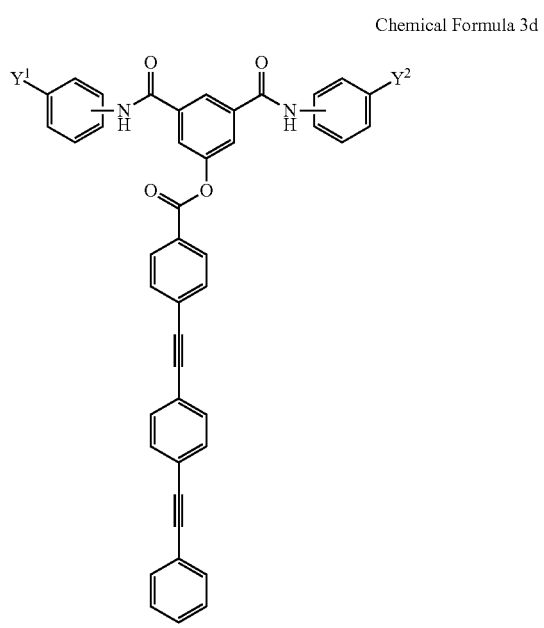
Chemical Formula 4b
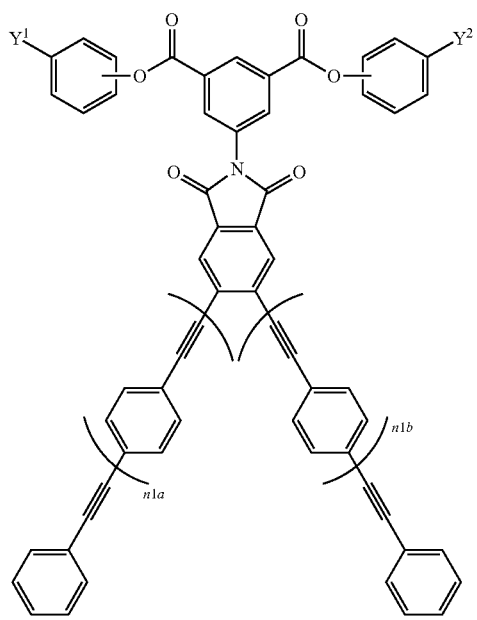
In Chemical Formulae 3a to 3d,
$Y^1$ and $Y^2$ are each independently OH or $NH_2$.
The monomer represented by Chemical Formula 4 may be represented by any one of Chemical Formulae 4a to 4d.

Chemical Formula 4c

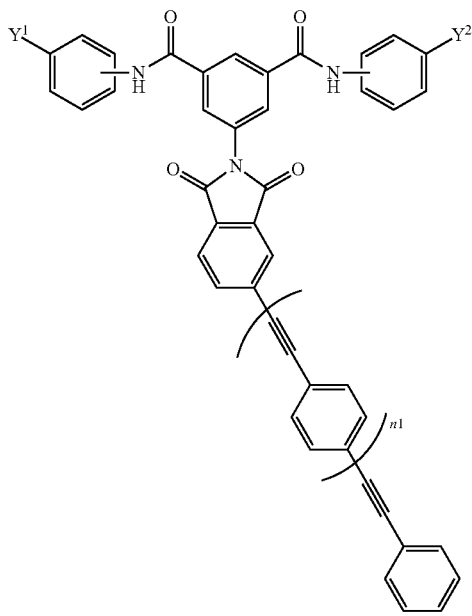

Chemical Formula 4d

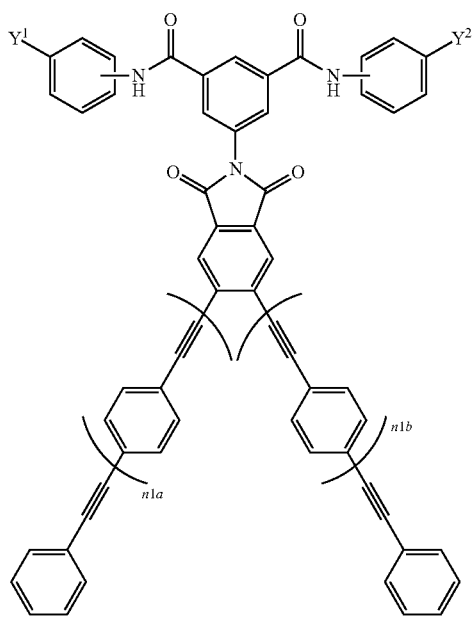

In Chemical Formulae 4a to 4d, $Y^1$ and $Y^2$ are each independently OH or $NH_2$, and n1, n1a, and n1b are each independently an integer ranging from 0 to 3.

According to another embodiment, a polymer having a first structural unit derived from the monomer is provided.

The first structural unit may be obtained from a reaction of the monomer and a carbonate compound or a reaction of the monomer and an anhydride compound.

The first structural unit may be represented by Chemical Formula 5.

Chemical Formula 5

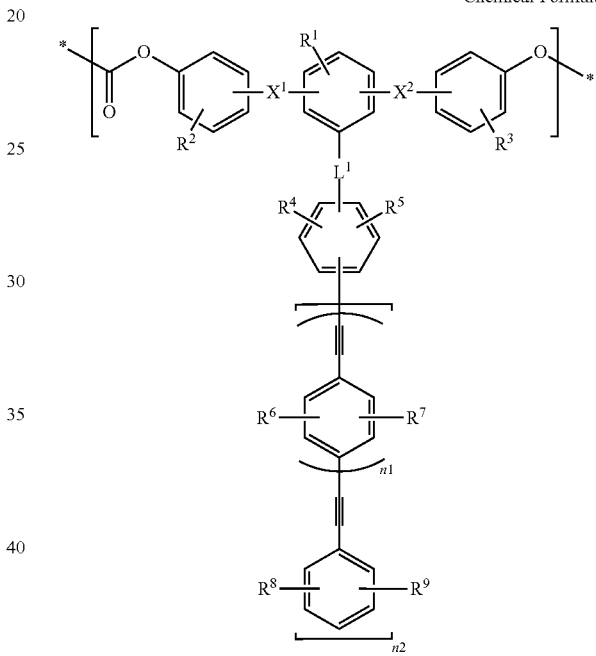

In Chemical Formula 5, $X^1$, $X^2$, and $L^1$ are each independently O, C(=O), C(=O)O, or C(=O)$NR^a$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, n2 is 1 or 2, and

* indicates a binding site to an adjacent atom.

The first structural unit may be represented by any one of Chemical Formulae 6 to 8.

Chemical Formula 6

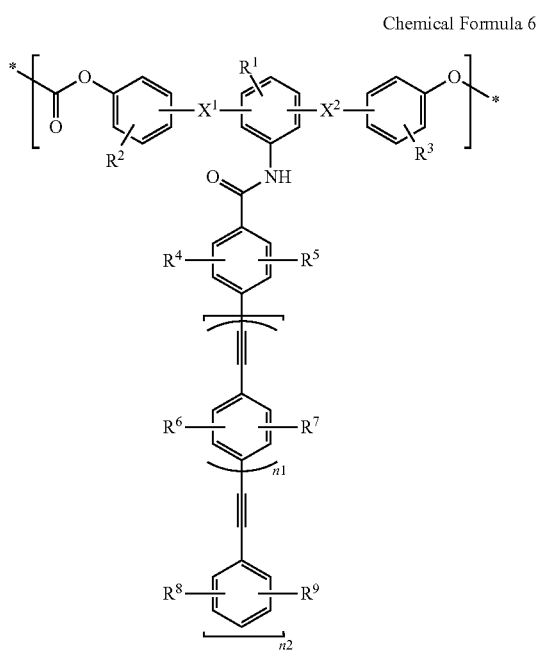

Chemical Formula 7

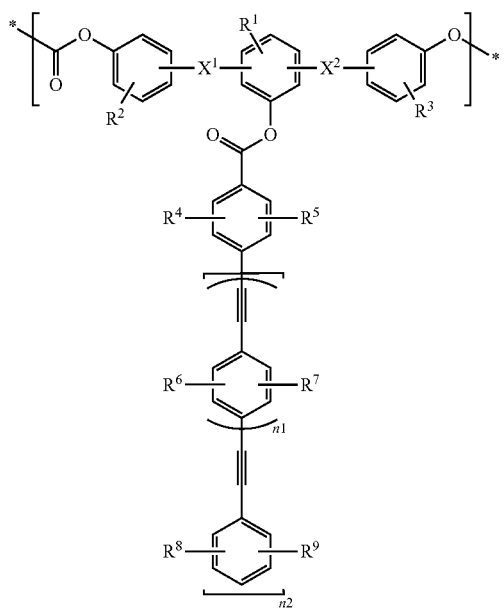

Chemical Formula 8

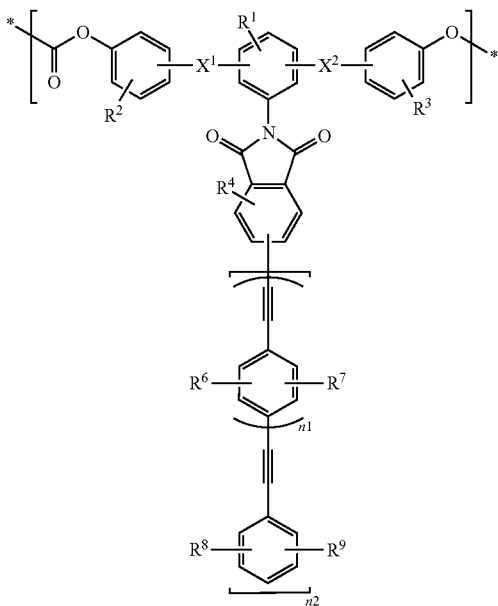

In Chemical Formulae 6 to 8, $X^1$ and $X^2$ are each independently O, C(=O), C(=O)O, or C(=O)NR$^a$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, n1 is an integer ranging from 0 to 3, n2 is 1 or 2, and

* indicates a binding site to an adjacent atom.

The first structural unit represented by Chemical Formula 6 may be represented by any one of Chemical Formulae 6a to 6d.

Chemical Formula 6a
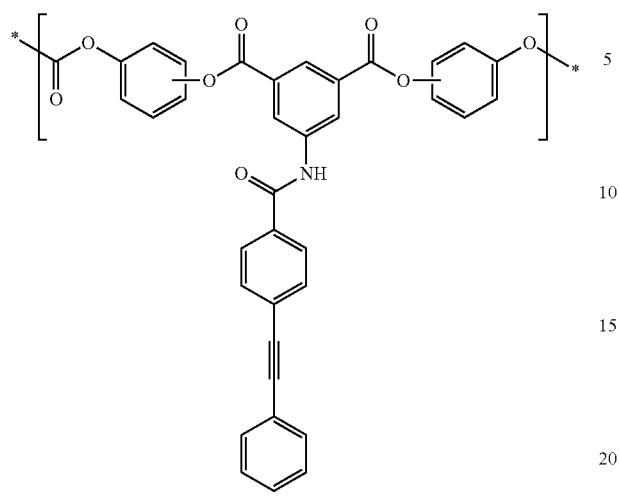
Chemical Formula 6b
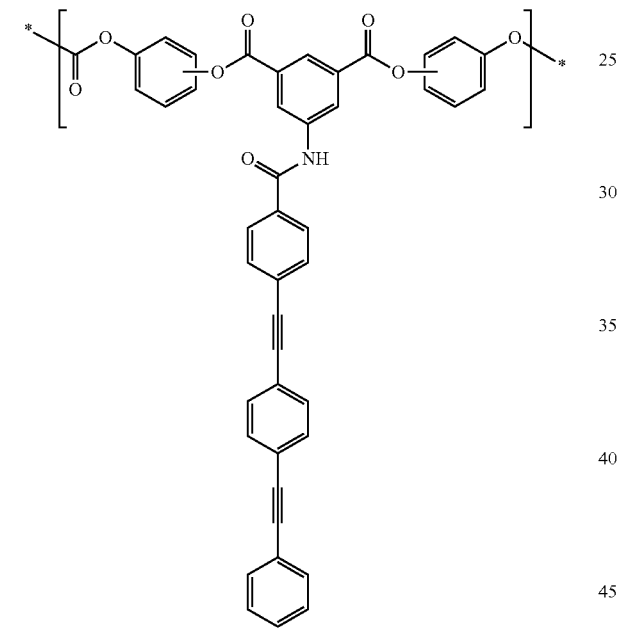
Chemical Formula 6c
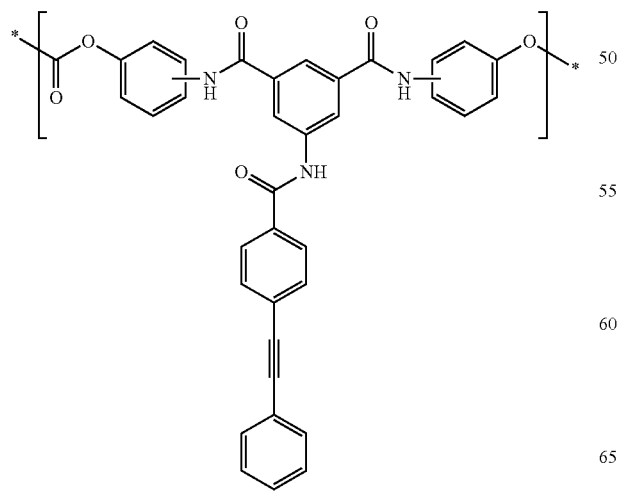
Chemical Formula 6d
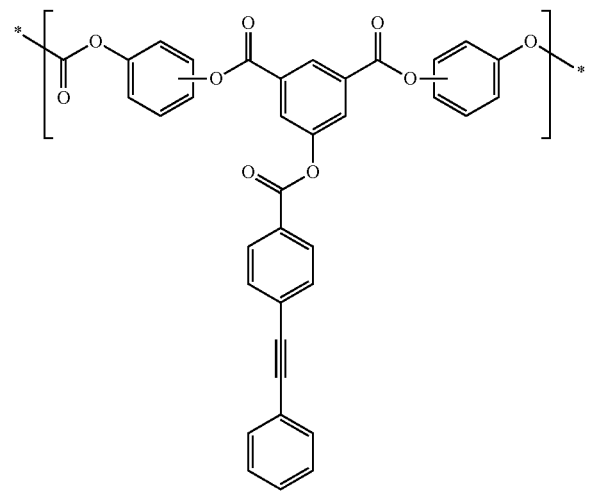
In Chemical Formulae 6a to 6d, * indicates a binding site to an adjacent atom.
The first structural unit represented by Chemical Formula 7 may be represented by any one of Chemical Formulae 7a to 7d.
Chemical Formula 7a Chemical Formula 7b
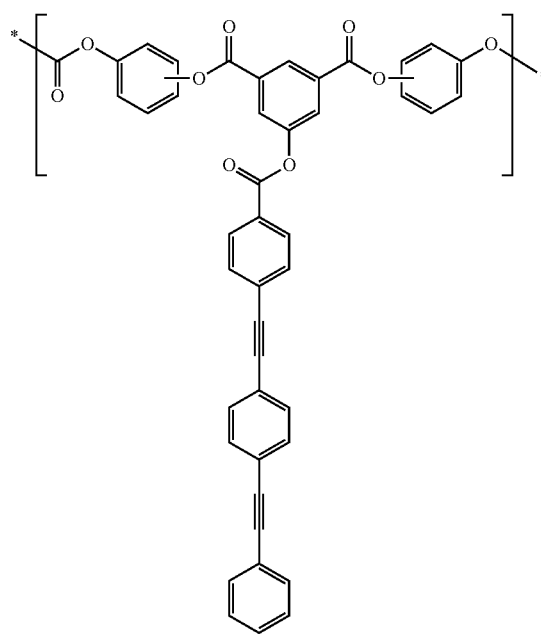
Chemical Formula 7c
Chemical Formula 7d
In Chemical Formulae 7a to 7d, * indicates a binding site to an adjacent atom.
The first structural unit represented by Chemical Formula 8 may be represented by any one of Formulae 8a to 8d.
Chemical Formula 8a
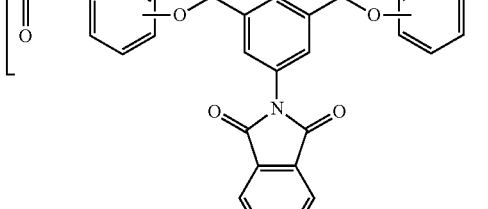

Chemical Formula 8b

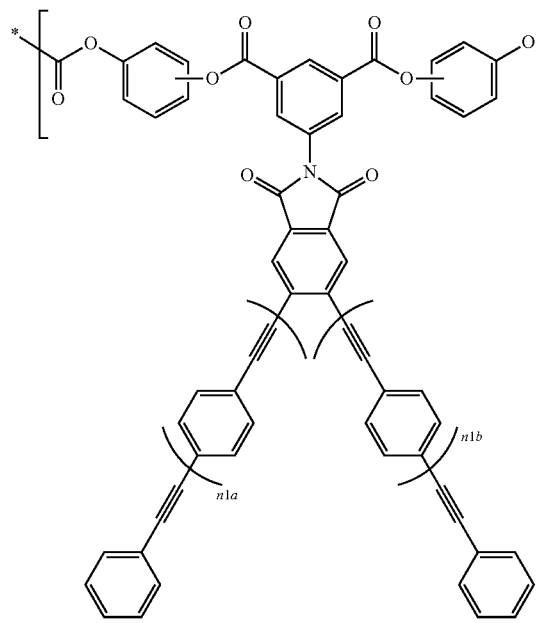

Chemical Formula 8d

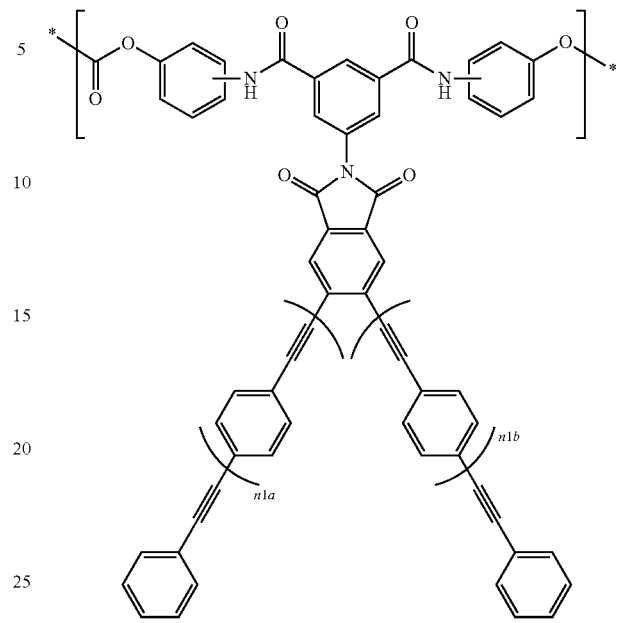

In Chemical Formulae 8a to 8d, n1, n1a and n1b are each independently an integer ranging from 0 to 3, and

* indicates a binding site to an adjacent atom.

The polymer may further include a second structural unit represented by Chemical Formula 9.

Chemical Formula 8c

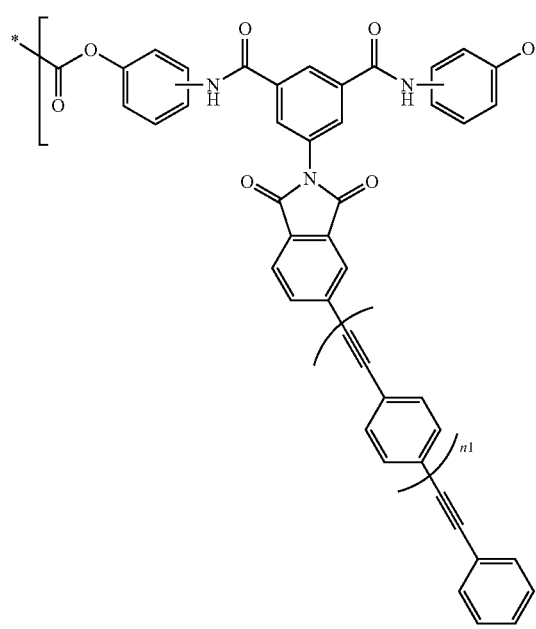

Chemical Formula 9

$$*\!\!-\!\!\left[\!\!\begin{array}{c}\text{O}\\\text{\Large\textbf{—}}\\\end{array}\!\!-\!\!\text{O}\!\!-\!\!\begin{array}{c}\\\text{\Large\textbf{—}}\\R^{16}\end{array}\!\!-\!\!L^3\!\!-\!\!\begin{array}{c}\\\text{\Large\textbf{—}}\\R^{17}\end{array}\!\!-\!\!\text{O}\!\!-\!\!\begin{array}{c}\text{O}\\\text{\Large\textbf{—}}\\\end{array}\!\!\right]\!\!-\!\!*$$

In Chemical Formula 9, $L^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO$_2$, or a combination thereof, $R^{16}$ and $R^{17}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

The first structural unit may be represented by Chemical Formula 10.

Chemical Formula 10

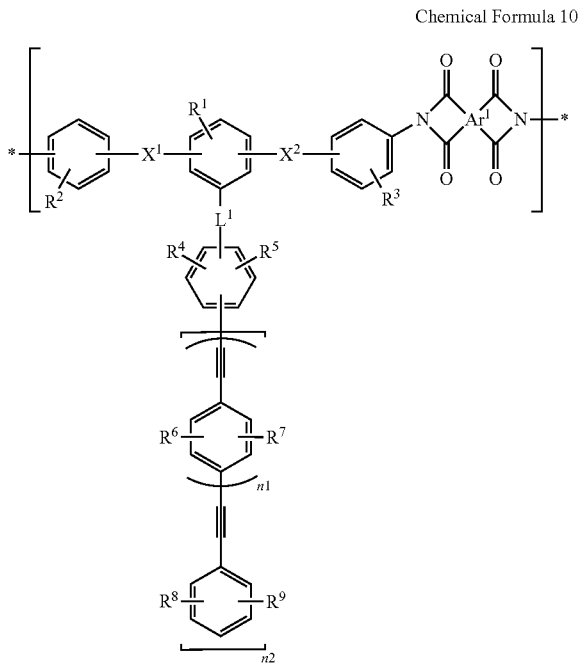

In Chemical Formula 10, $X^1$, $X^2$, and $L^1$ are each independently O, C(=O), C(=O)O, or C(=O)NR$^a$, $Ar^1$ is a substituted or unsubstituted C6 to C30 arylene group, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, n2 is 1 or 2, and

* indicates a binding site to an adjacent atom.

The first structural unit represented by Chemical Formula 10 may be represented by any one of Chemical Formulae 11 to 16.

Chemical Formula 11

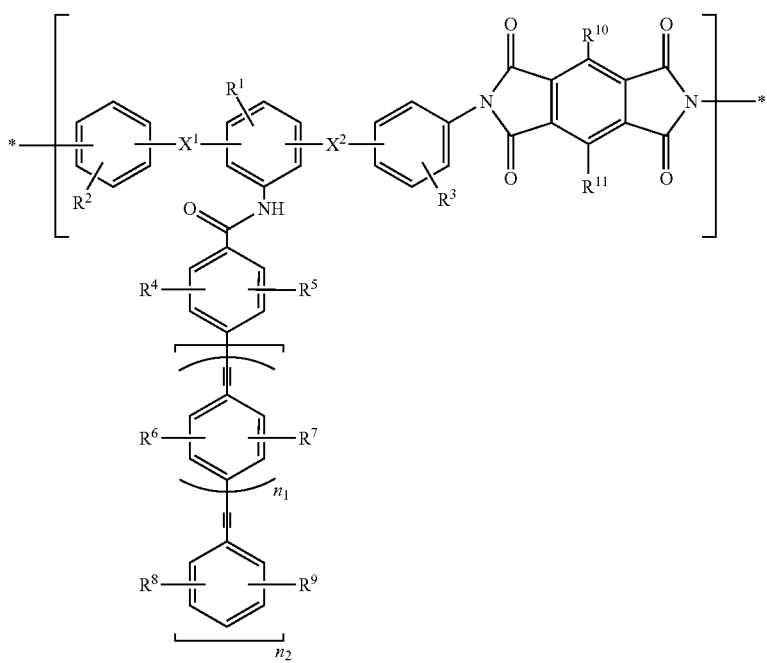

Chemical Formula 12
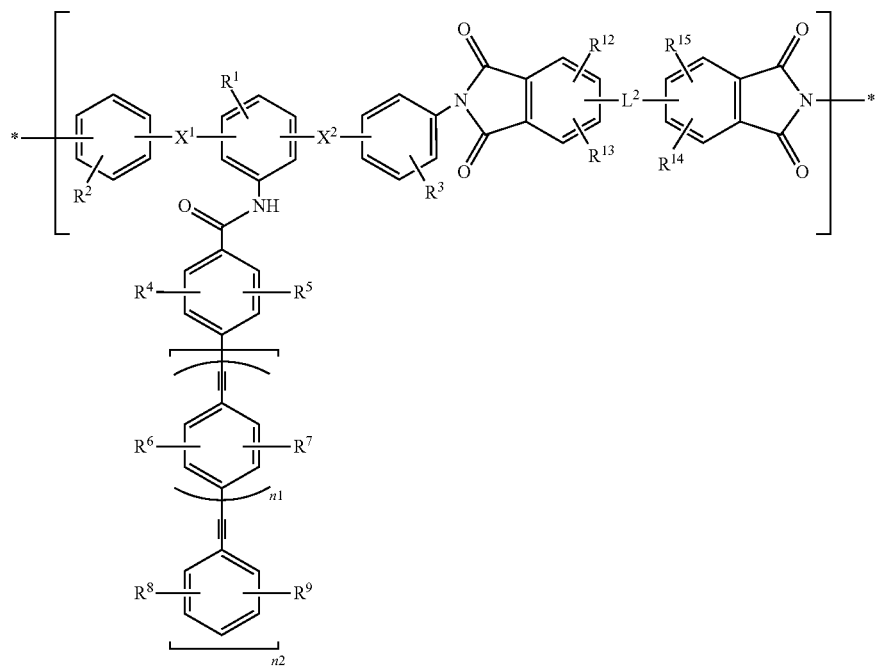
Chemical Formula 13
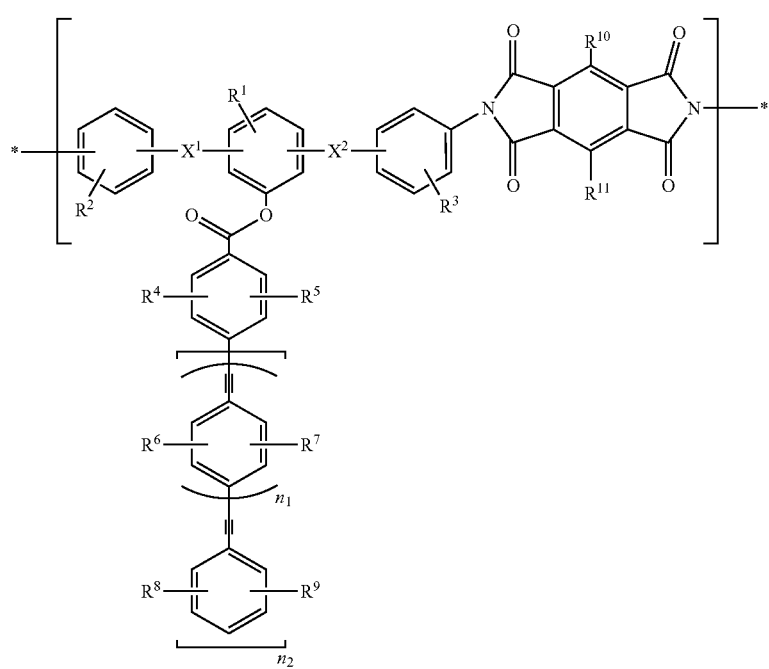

-continued
Chemical Formula 14
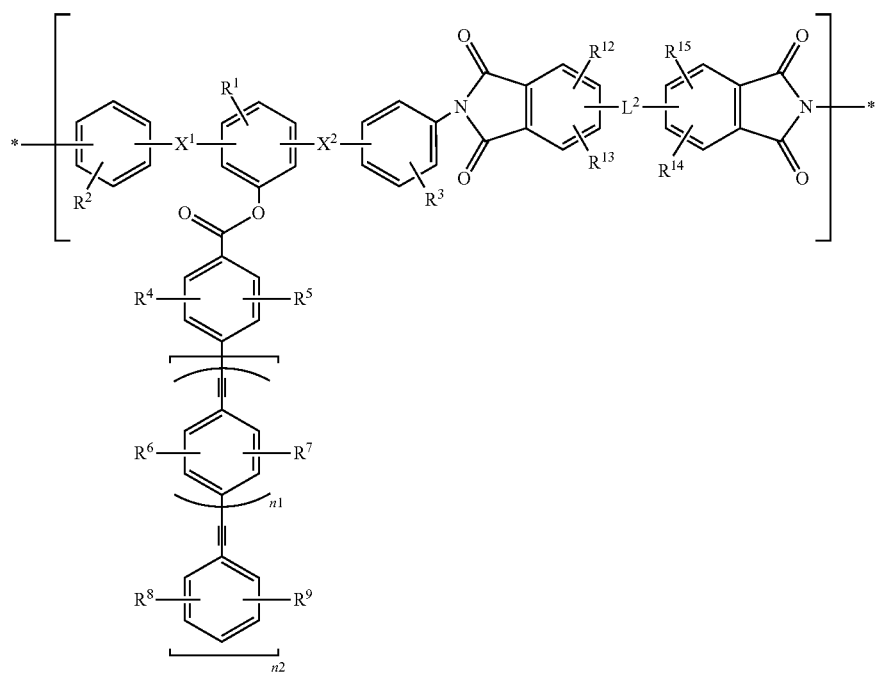
Chemical Formula 15
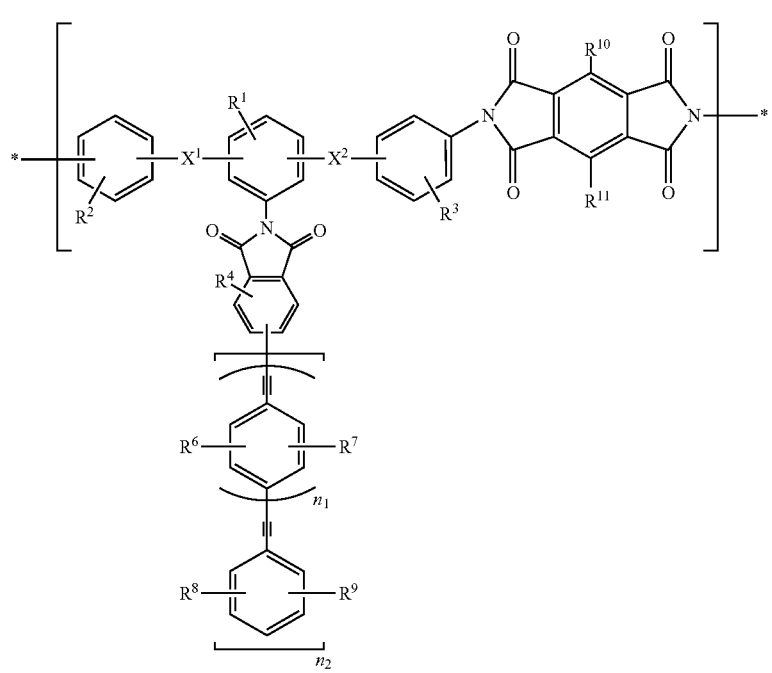

Chemical Formula 16

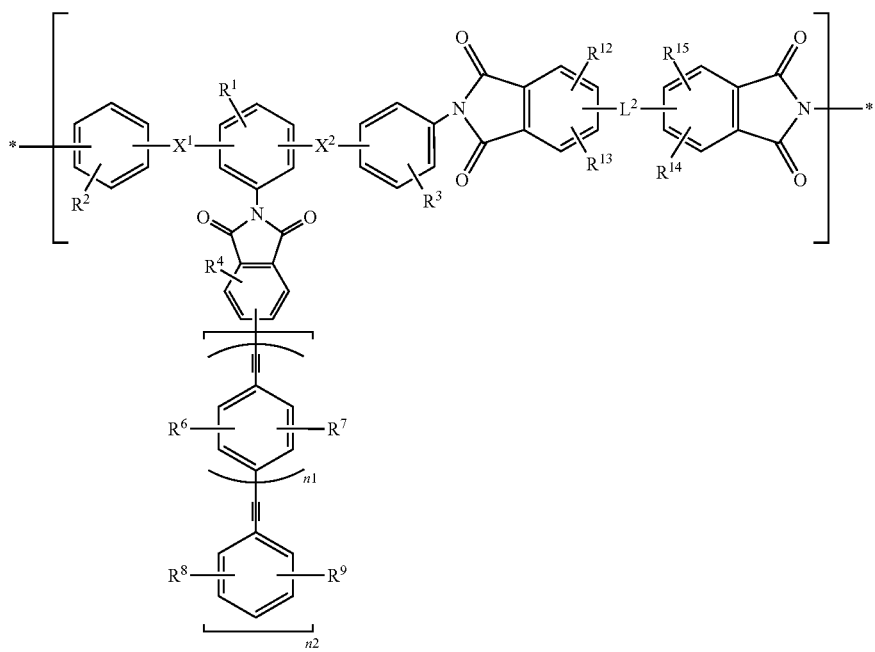

In Chemical Formulae 1 to 16, * indicates a binding site to an adjacent atom.

The polymer may further include a second structural unit represented by Chemical Formula 17 or 18.

Chemical Formula 17

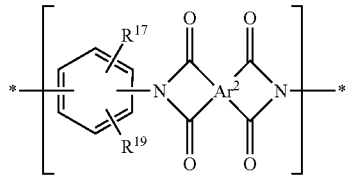

Chemical Formula 18

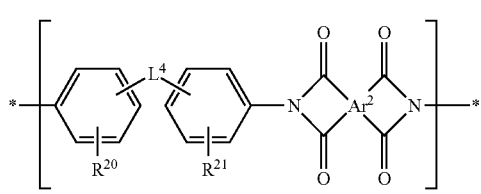

In Chemical Formula 17 or 18, $Ar^2$ is a substituted or unsubstituted C6 to C30 arylene group, $L^4$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO₂, or a combination thereof, $R^{18}$ to $R^{21}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

According to another embodiment, a compensation film including the polymer is provided.

According to another embodiment, an optical film including the compensation film and polarizer is provided.

According to another embodiment, a display device including the compensation film or the optical film is provided.

BRIEF DESCRIPTION OF THE DRAWINGS

These and/or other aspects will become apparent and more readily appreciated from the following description of the embodiments, taken in conjunction with the accompanying drawings, in which.

DETAILED DESCRIPTION

Figure 1:
FIG. 1 is a schematic cross-sectional view showing an optical film according to an embodiment.

Exemplary embodiments of the present disclosure will hereinafter be described in detail, and may be readily performed by person having an ordinary skill in the related art. However, this disclosure may be embodied in many different forms, and is not construed as limited to the exemplary embodiments set forth herein.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise. The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, the term 'substituted' refers to a group or atom substituted with at least one substituent selected from a halogen, a hydroxy group, an alkoxy group, a nitro group, a cyano group, an amino group, an azido group, an amidino group, a hydrazino group, a hydrazono group, a carbonyl group, a carbamoyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof, instead of hydrogen of a compound.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "alkoxy group" refers to "alkyl-O—", wherein the term "alkyl" has the same meaning as described above.

As used herein, when a definition is not otherwise provided, the term "cycloalkyl group" refers to a monovalent group having one or more saturated rings in which all ring members are carbon.

As used herein, when a definition is not otherwise provided, the term "aryl", which is used alone or in combination, refers to an aromatic hydrocarbon containing at least one ring and having the specified number of carbon atoms.

The term "aryl" may be construed as including a group with an aromatic ring fused to at least one cycloalkyl ring.

As used herein, when a definition is not otherwise provided, the term "heterocyclic group" refers to a monovalent group having one or more saturated rings including one to three heteroatom ring members selected from the group consisting of N, O, S, Se, and P, wherein the remaining ring members are carbon.

As used herein, when a definition is not otherwise provided, the term "silyl group" refers to a groups having formula —SiR$_3$, wherein R is each independently selected from an alkyl group and an aryl group as defined above.

As used herein, when a definition is not otherwise provided, the term "halogen" refers to fluorine, chlorine, bromine, and iodine.

As used herein, when a definition is not otherwise provided, the term "hydroxy group" refers to "—OH".

As used herein, when a definition is not otherwise provided, the term "nitro group" refers to "—NO$_2$".

As used herein, when a definition is not otherwise provided, the term "hydrocarbonyl group" refers to "—C(=O)H".

As used herein, when a definition is not otherwise provided, the term "alkanoyl" refers to "alkyl-C(=O)—", wherein the term "alkyl" is the same as defined above.

As used herein, the term "alkylene group" refers to a straight or branched saturated aliphatic hydrocarbon group having a valence of at least two, optionally substituted with one or more substituents where indicated, provided that the valence of the alkylene group is not exceeded.

As used herein, the term "cycloalkylene group" refers to a cyclic hydrocarbon group having a valence of at least two, optionally substituted with one or more substituents where indicated, provided that the valence of the cycloalkylene group is not exceeded.

As used herein, when a definition is not otherwise provided, the term "arylene group" refers to a functional group having a valence of at least two obtained by removal of two hydrogens in an aromatic ring, optionally substituted with one or more substituents where indicated, provided that the valence of the alkylene group is not exceeded.

As used herein, the term "divalent heterocyclic group" refers to a cyclic group having a valence of at least two, optionally substituted with one or more substituents where indicated, and including one to three heteroatom ring members selected from the group consisting of N, O, S, Se, and P, wherein the remaining ring members are carbon, provided that the valence of the divalent heterocyclic group is not exceeded.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C1 to C30 alkyl" refers to a C1 to C30 alkyl group substituted with C6 to C30 aryl group, the total number of carbon atoms in the resulting aryl substituted alkyl group is C7 to C60.

As used herein, when a definition is not otherwise provided, the term 'hetero' refers to one including 1 to 3 hetero atoms selected from N, O, S, Se, and P.

Hereinafter, a monomer according to an embodiment is described.

A monomer according to an embodiment is represented by Chemical Formula 1.

Chemical Formula 1

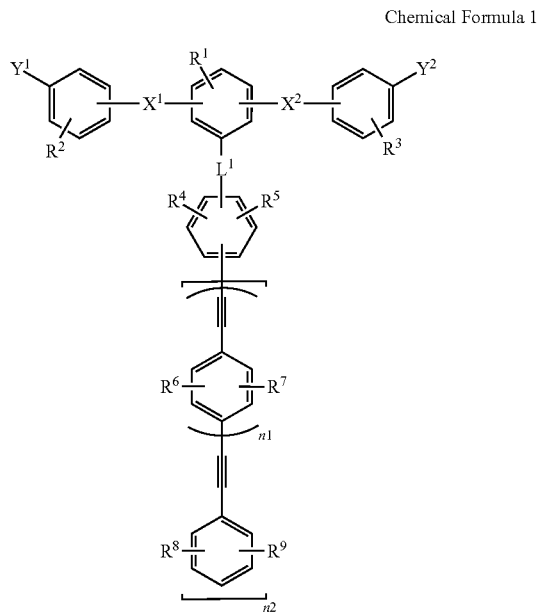

In Chemical Formula 1, $X^1$, $X^2$, and $L^1$ are each independently O, C(=O), C(=O)O, or C(=O)$NR^a$, $Y^1$ and $Y^2$ are each independently OH or $NH_2$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, and n2 is 1 or 2.

The monomer has a phenylacetylene group that is consecutively linked in one direction and may effectively absorb light in a predetermined wavelength region due to the presence of the phenylacetylene group. Accordingly, it may be applied to various devices requiring good optical properties.

For example, the monomer may react with an aliphatic or aromatic mesogen compound and may be used as a liquid crystal material having desirable optical properties.

For example, the monomer may react with a carbonate or a derivative thereof such as triphosgene to form a polycarbonate. The polycarbonate film may be, for example used as a compensation film having desirable optical properties.

For example, the monomer may react with anhydride to provide polyamic acid and/or polyimide. The polyamic acid film and/or polyimide film may be, for example used as a compensation film having desirable optical properties.

In addition, the monomer may have improved solubility and may be synthesized by a readily available synthesis method.

For example, in Chemical Formula 1, $X^1$ and $X^2$ may be the same.

For example, in Chemical Formula 1, $Y^1$ and $Y^2$ may be the same.

For example, in Chemical Formula 1, $R^1$ to $R^9$ may independently be hydrogen.

For example, in Chemical Formula 1, n1 may be 0 or 1.

The monomer may be, for example represented by any one of Chemical Formulae 2 to 4.

Chemical Formula 2

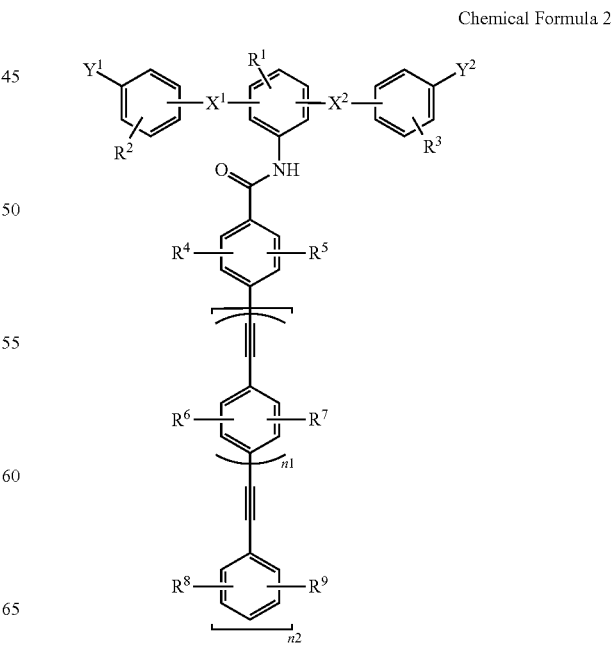

Chemical Formula 3

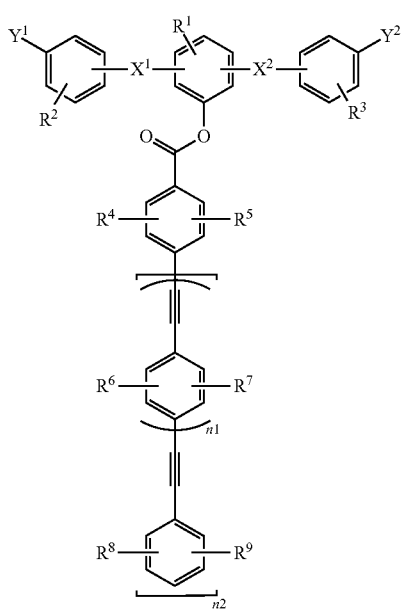

Chemical Formula 2a

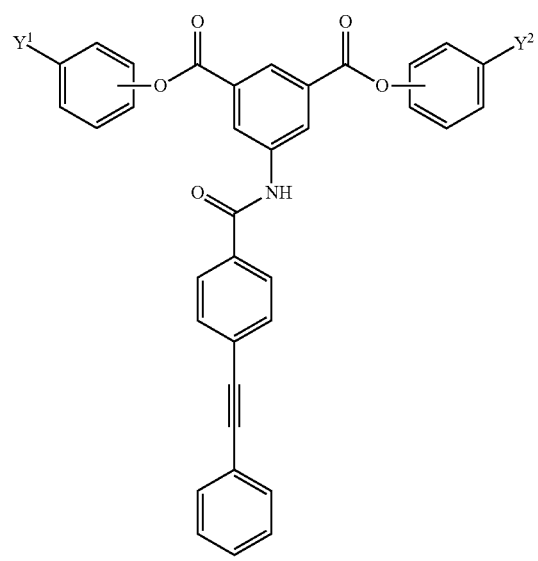

Chemical Formula 4

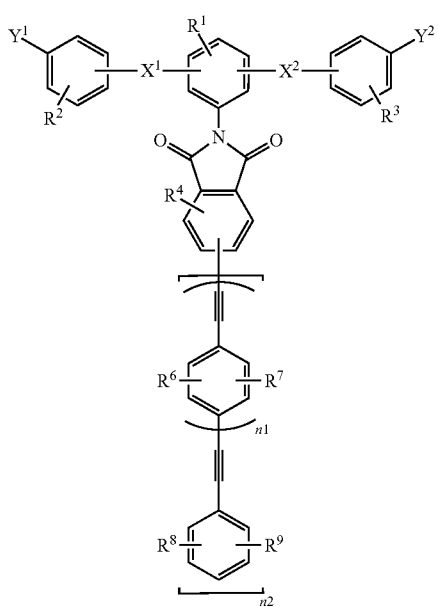

Chemical Formula 2b

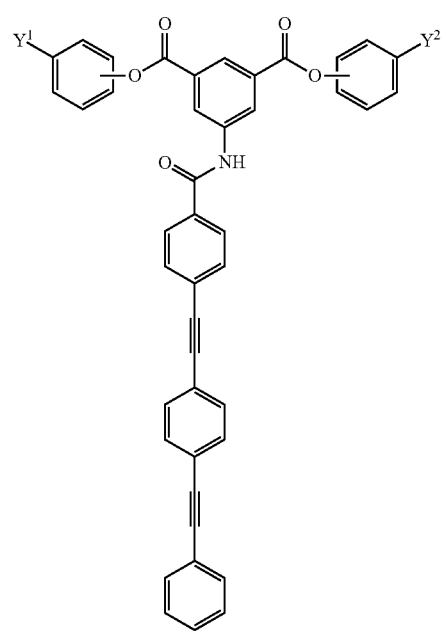

In Chemical Formulae 2 to 4, $X^1$, $X^2$, $Y^1$, $Y^2$, $R^1$ to $R^9$, n1, and n2 are the same as described above.

For example, in Chemical Formulae 2 to 4, $X^1$ and $X^2$ may be the same.

For example, in Chemical Formulae 2 to 4, $R^1$ to $R^9$ may independently be hydrogen.

For example, in Chemical Formulae 2 to 4, n1 may be 0 or 1.

The monomer represented by Chemical Formula 2 may be, for example represented by any one of Chemical Formulae 2a to 2d, but is not limited thereto.

Chemical Formula 2c
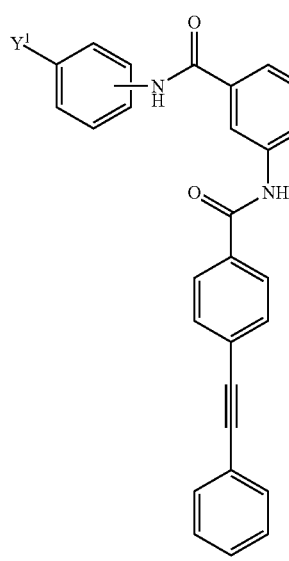
Chemical Formula 3a
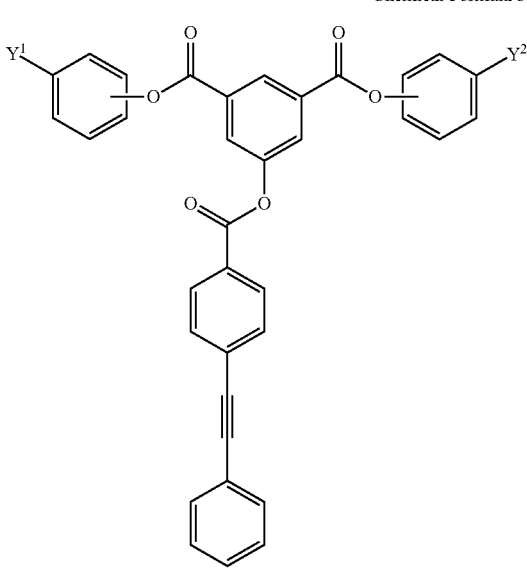
Chemical Formula 2d
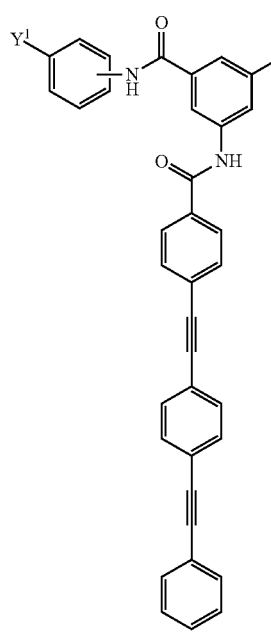
Chemical Formula 3b
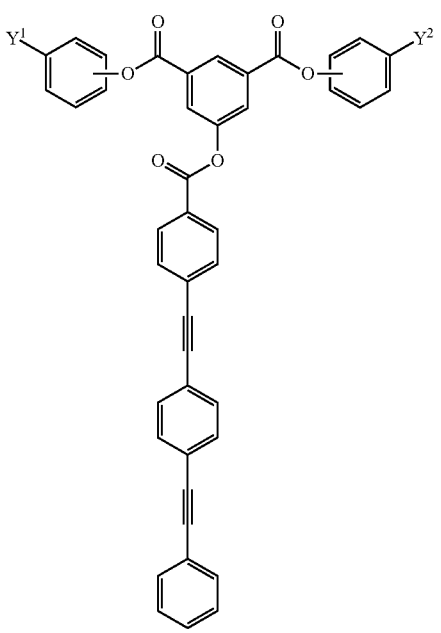
In Chemical Formulae 2a to 2d, $Y^1$ and $Y^2$ are the same as described above.
The monomer represented by Chemical Formula 3 may be, for example represented by any one of Chemical Formulae 3a to 3d, but is not limited thereto.

Chemical Formula 3c
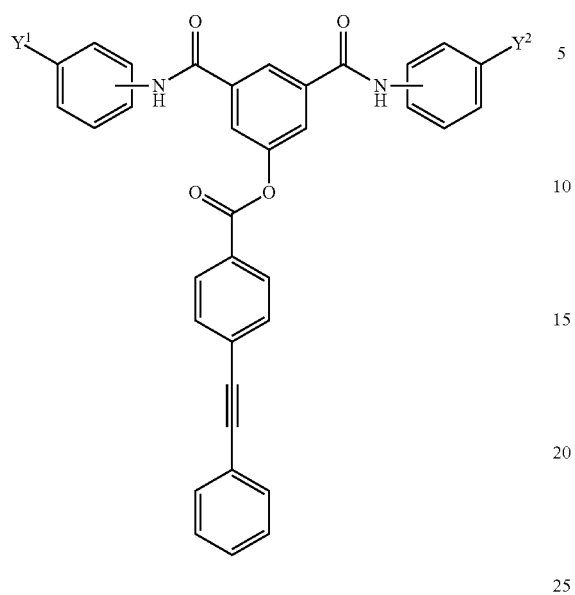
Chemical Formula 4a
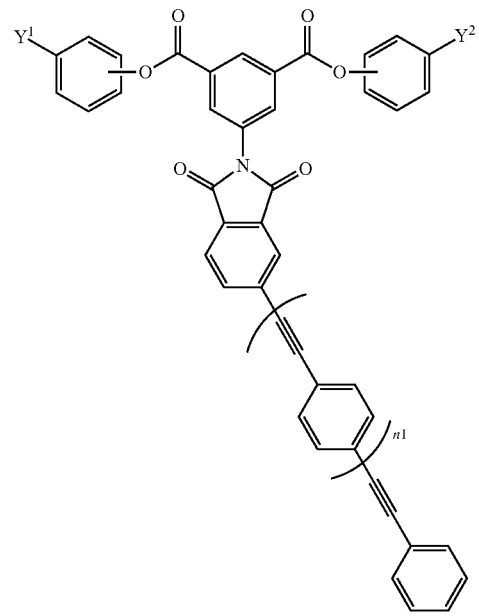
Chemical Formula 3d
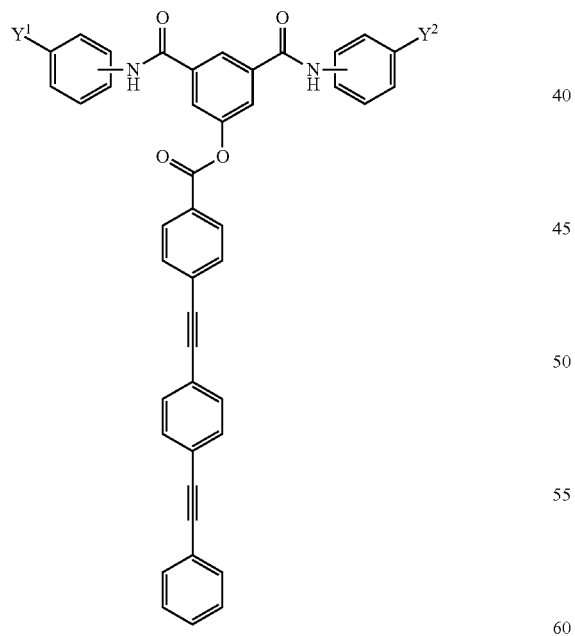
Chemical Formula 4b
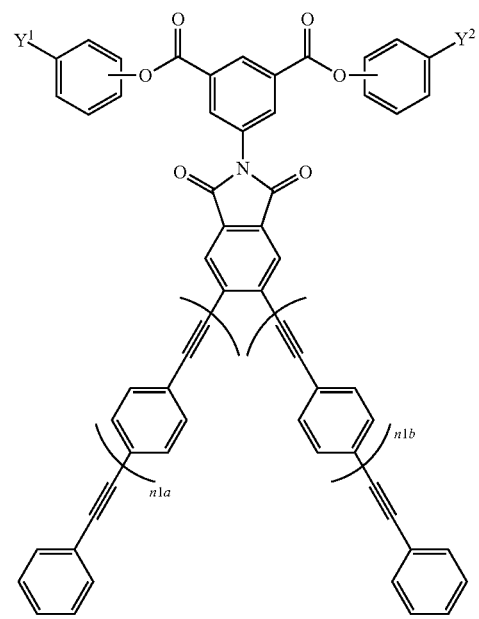
In Chemical Formulae 3a to 3d, $Y^1$ and $Y^2$ are the same as described above.
The monomer represented by Chemical Formula 4 may be, for example represented by any one of Chemical Formulae 4a to 4d, but is not limited thereto.

Chemical Formula 4c

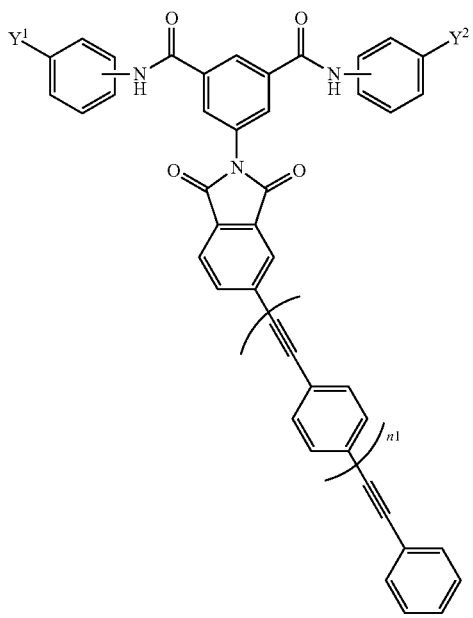

Chemical Formula 4d

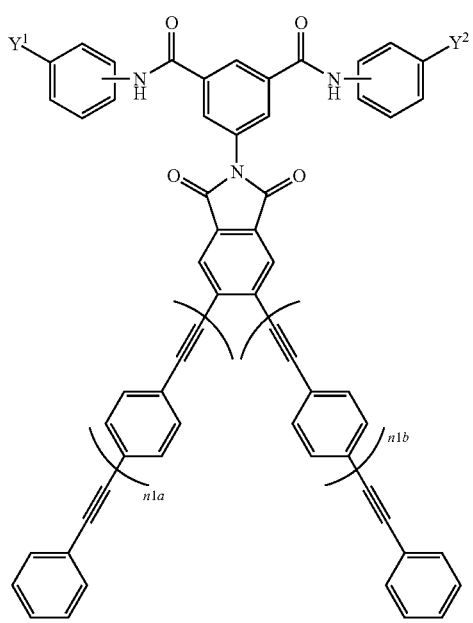

In Chemical Formulae 4a to 4d, $Y^1$, $Y^2$, and n1 are the same as described above, and n1a and n1b are each independently integers of 0 to 3.

For example, in Chemical Formulae 4a to 4d, n1, n1a, and n1b may independently be 0 or 1.

The monomer may form a homopolymer or a copolymer with another monomer. The polymer may have a structural unit derived from the monomer represented by Chemical Formula 1.

The monomer may react with a carbonate or a derivative thereof to form a polycarbonate including a structural unit derived from the monomer represented by Chemical Formula 1.

The polycarbonate may include, for example a first structural unit represented by Chemical Formula 5.

Chemical Formula 5

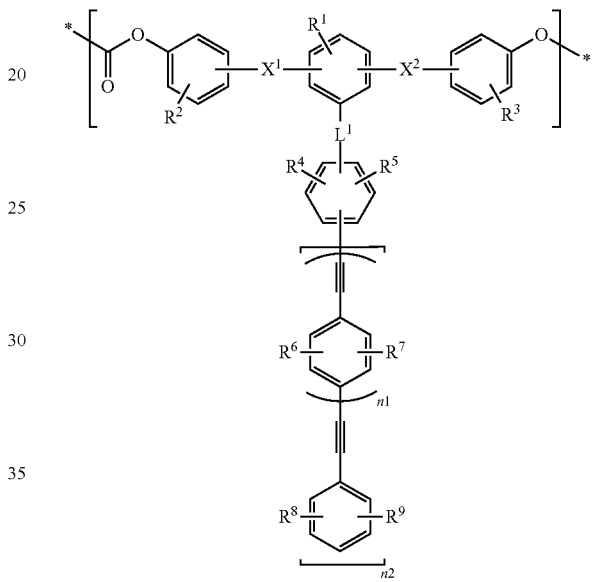

In Chemical Formula 5, $X^1$, $X^2$, $L^1$, $R^1$ to $R^9$, n1, and n2 are the same as described above.

The first structural unit represented by Chemical Formula 5 may include a main chain moiety obtained by a reaction of the monomer with a carbonate or a derivative thereof, and a side chain of a phenylacetylene group arranged with respect to the main chain moiety in a substantially perpendicular direction. Accordingly, light absorption characteristics depending on a refractive index and a wavelength of the main chain and the side chain of the polymer may be changed by selecting an appropriate position and number of the phenylacetylene group. Accordingly, the polymer may be applied to various fields that required good optical properties. For example, the polymer may control birefringence depending on a wavelength by controlling a refractive index in a main chain direction and a refractive index in a side chain direction.

For example, in Chemical Formula 5, $X^1$ and $X^2$ may be the same.

For example, in Chemical Formula 5, $R^1$ to $R^9$ may independently be hydrogen.

For example, in Chemical Formula 5, n1 may be 0 or 1.

The first structural unit represented by Chemical Formula 5 may be, for example represented by any one of Chemical Formulae 6 to 8.

Chemical Formula 6
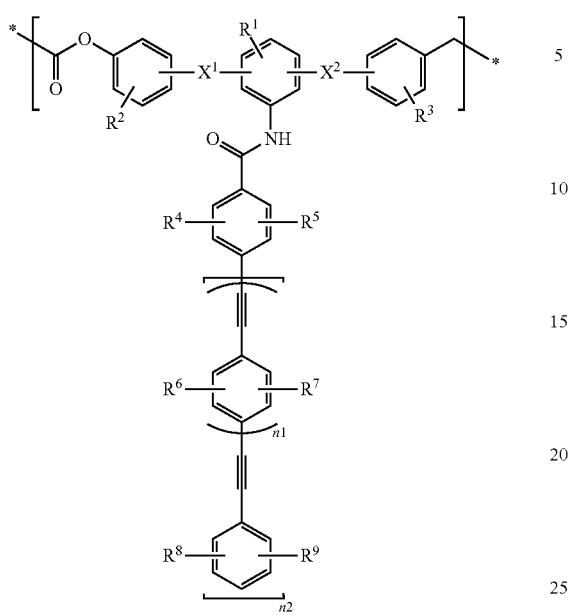
Chemical Formula 7
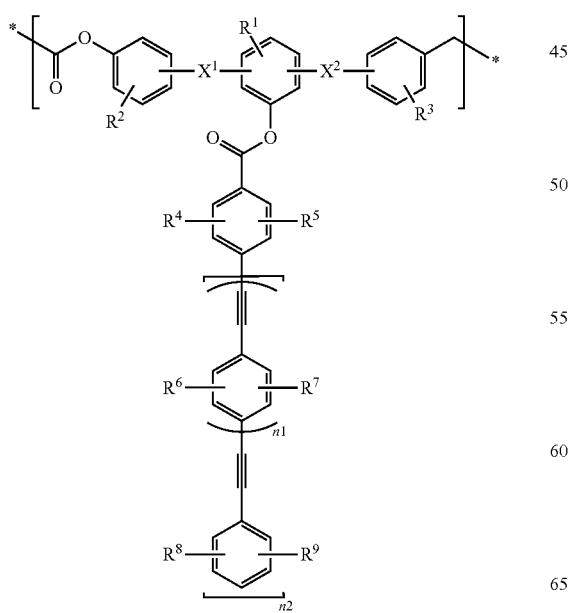
Chemical Formula 8
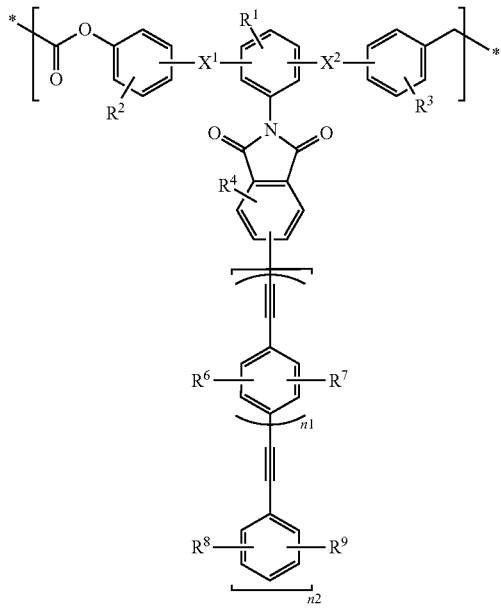
In Chemical Formulae 6 to 8,
$X^1$, $X^2$, $R^1$ to $R^9$, n1, and n2 are the same as described above, and
\* indicates a binding site to an adjacent atom.
The first structural unit represented by Chemical Formula 6 may be, for example represented by any one of Chemical Formulae 6a to 6d, but is not limited thereto.
Chemical Formula 6a
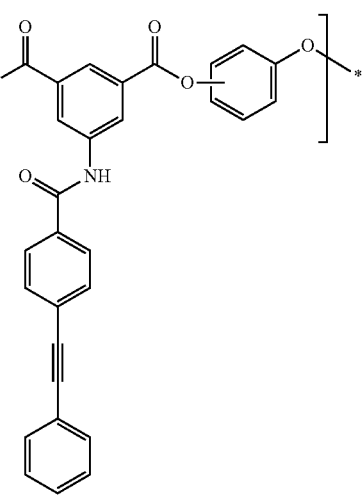

Chemical Formula 6b
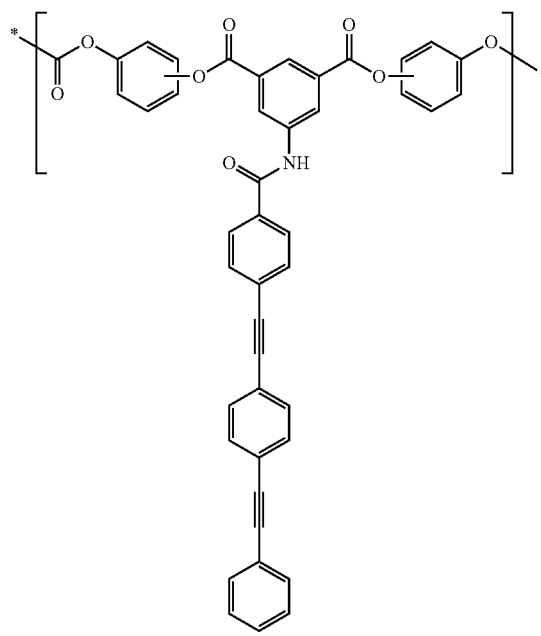
Chemical Formula 6d
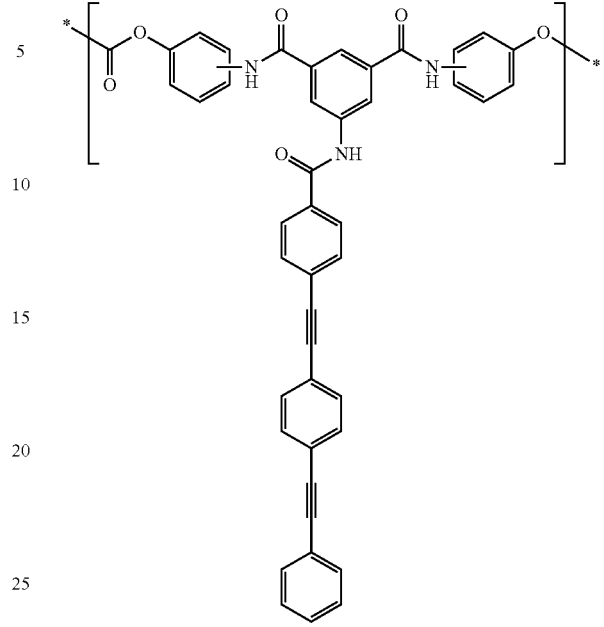
In Chemical Formulae 6a to 6d, * indicates a binding site to an adjacent atom.
The first structural unit represented by Chemical Formula 7 may be, for example represented by any one of Chemical Formulae 7a to 7d, but is not limited thereto.
Chemical Formula 6c
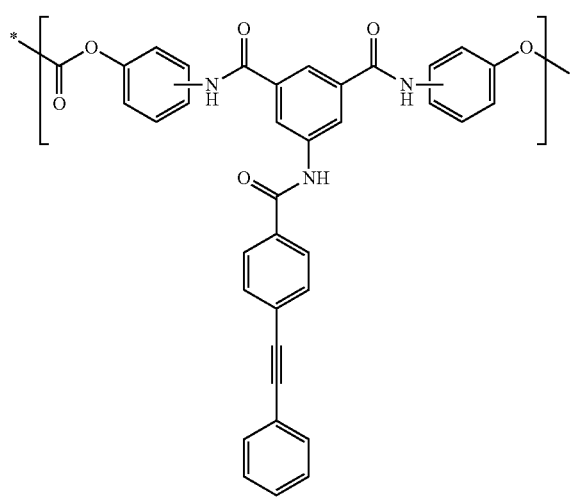
Chemical Formula 7a
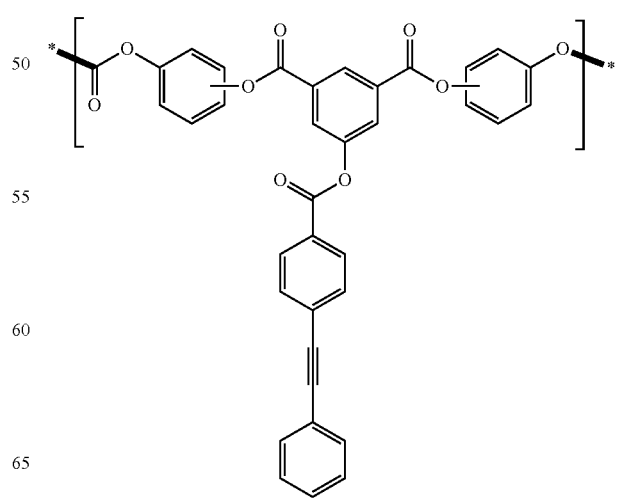

Chemical Formula 7b
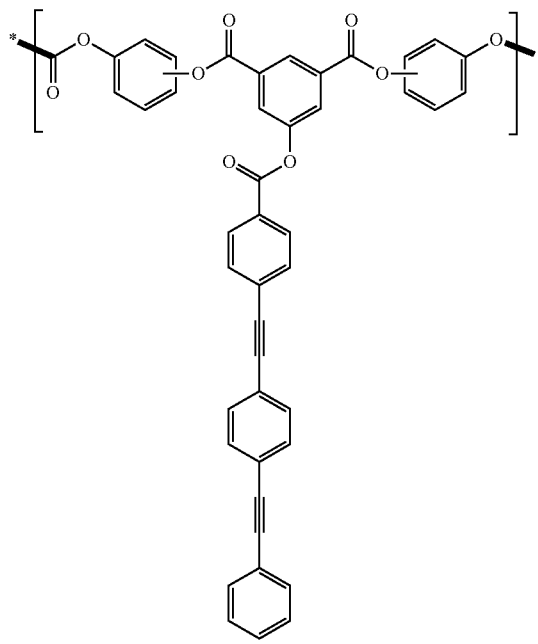
Chemical Formula 7c
Chemical Formula 7d
In Chemical Formulae 7a to 7d, * indicates a binding site to an adjacent atom.
The first structural unit represented by Chemical Formula 8 may be, for example represented by any one of Chemical Formulae 8a to 8d, but is not limited thereto.
Chemical Formula 8a Chemical Formula 8b

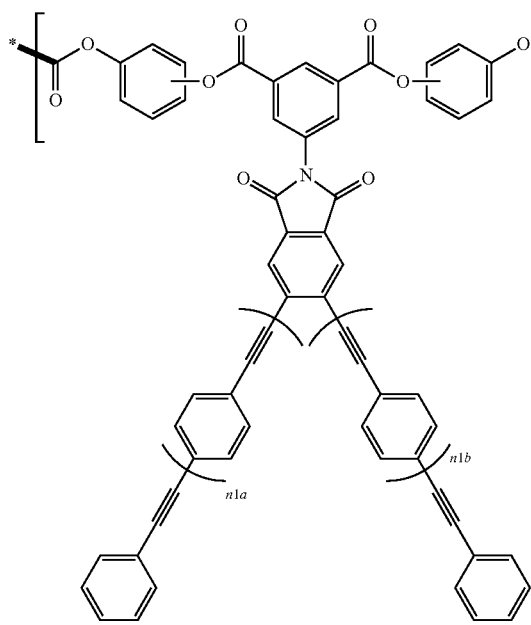

Chemical Formula 8d

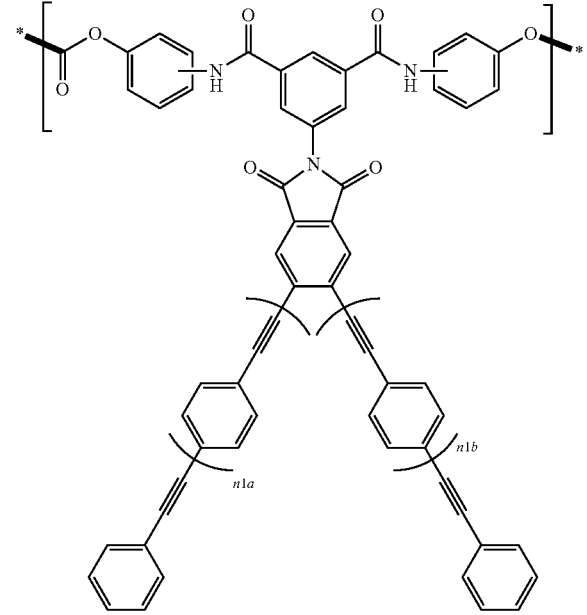

Chemical Formula 8c

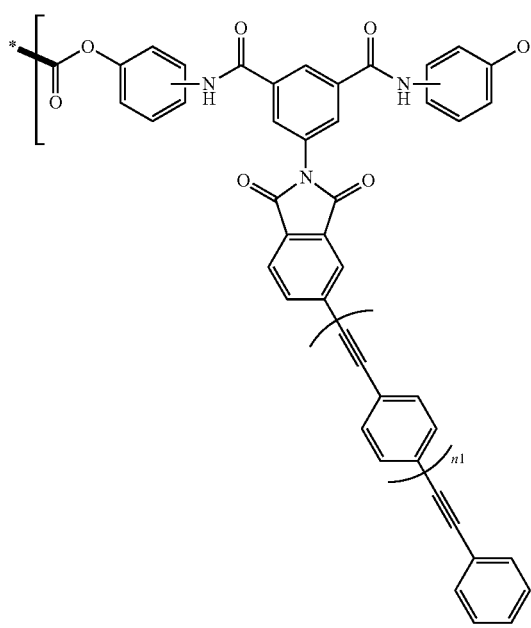

In Chemical Formulae 8a to 8d, n1, n1a, n1b, and * are the same as described above.

The polycarbonate may be obtained by copolymerizing at least one other monomer in addition to the monomer represented by Chemical Formula 1, and may further include at least one structural unit derived from the at least one other monomer. The other monomer may have a reaction site that is capable of reacting with the carbonate or the derivative thereof during polymerization to form a polycarbonate having a carbonate group. The other monomer may be, for example a monomer having a hydroxy group, and may be, for example bisphenol or a derivative thereof, but is not limited thereto.

For example, when the bisphenol or the derivative thereof is polymerized together, the polymer may further include a second structural unit represented by Chemical Formula 9 in addition to the first structural unit represented by Chemical Formula 5.

Chemical Formula 9

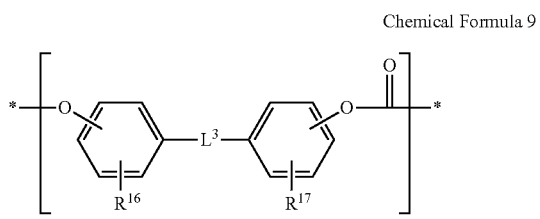

In Chemical Formula 9, $L^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or combination thereof, $R^{16}$ and $R^{17}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

The second structural unit may have a main chain moiety obtained by a reaction of the bisphenol or a derivative thereof with the carbonate or a derivative thereof.

When the polycarbonate includes the first structural unit and the second structural unit, the first structural unit and the second structural unit may be included in a mole ratio of about 0.1:99.9 to about 99.9 to 0.1. While not wishing to be bound by theory, it is understood that within the above ranges, flexibility may be fortified while desirable optical properties may be attained, and thus, the polycarbonate may be readily transformed into a film. Within the above ranges, the first and second structural units may be, for example, included in a mole ratio of about 0.1:99.9 to about 10.0:90.0, for example about 0.5:99.5 to about 10:90, for example about 1:99 to about 10:99.

The monomer may react with anhydride to provide a polyamic acid and/or polyimide including a structural unit derived from the monomer represented by Chemical Formula 1.

The polyimide may include, for example a first structural unit represented by Chemical Formula 10.

Chemical Formula 10

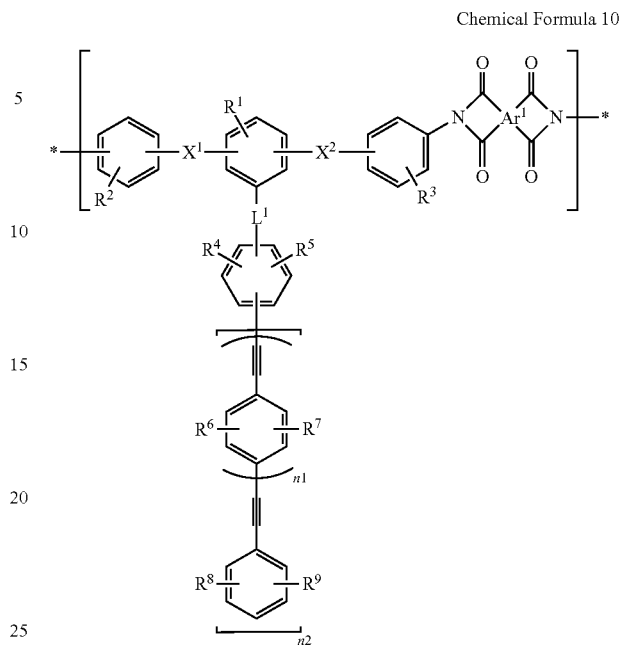

in Chemical Formula 10, $X^1$, $X^2$, $L^1$, $R^1$ to $R^9$, n1, and n2 are the same as described above, $Ar^1$ is a substituted or unsubstituted C6 to C30 arylene group, and

* indicates a binding site to an adjacent atom.

The polyimide may have a polyimide main chain and a side chain containing a phenylacetylene group, which is arranged with respect to the polyimide main chain in a substantially perpendicular direction. Accordingly, a refractive index and light absorption characteristics of the main chain and the side chain depending on a wavelength may be changed by controlling the positions and the numbers of the phenylacetylene group.

Accordingly, the polymer may be applied to various fields that need good optical properties. For example, the polymer may control birefringence depending on a wavelength by controlling a refractive index in a main chain direction and a refractive index in a side chain direction.

For example, in Chemical Formula 10, $X^1$ and $X^2$ may be the same.

For example, in Chemical Formula 10, $R^1$ to $R^9$ may independently be hydrogen.

For example, in Chemical Formula 10, n1 may be 0 or 1.

The first structural unit represented by Chemical Formula 10 may be, for example represented by any one of Chemical Formulae 11 to 16.

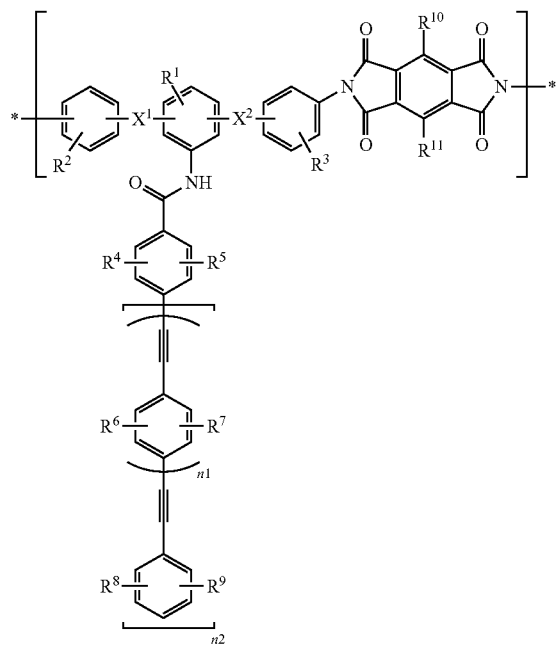
Chemical Formula 11
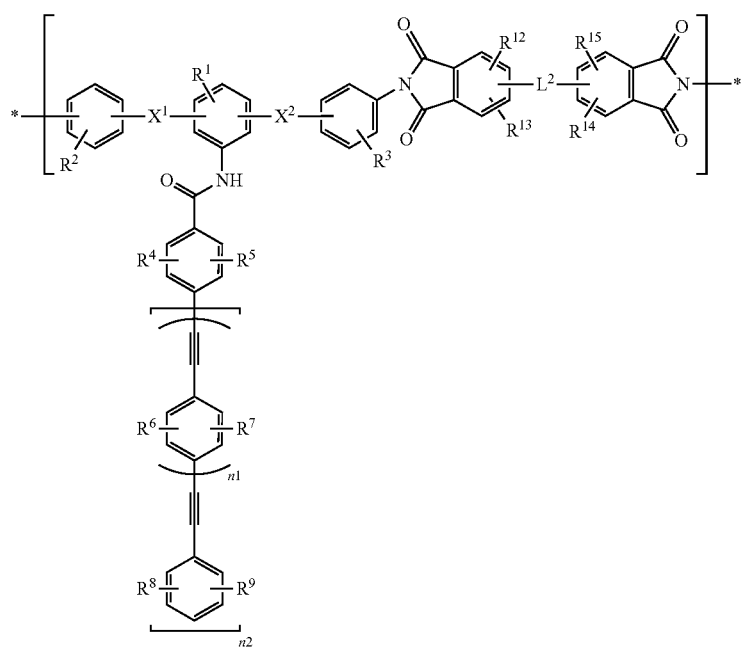
Chemical Formula 12

-continued
Chemical Formula 13
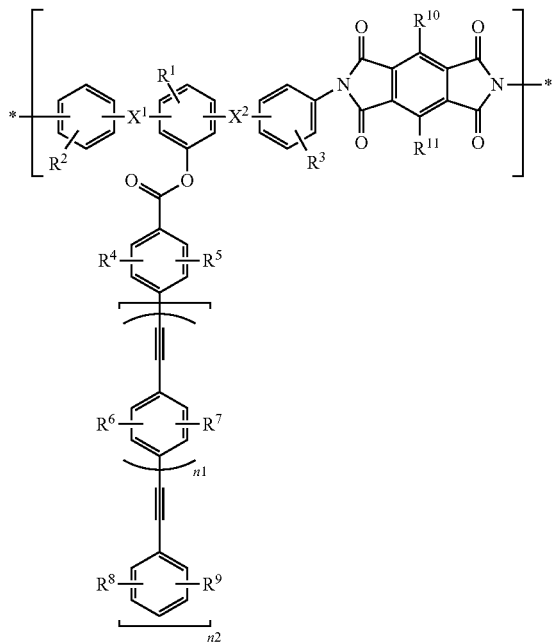
Chemical Formula 14
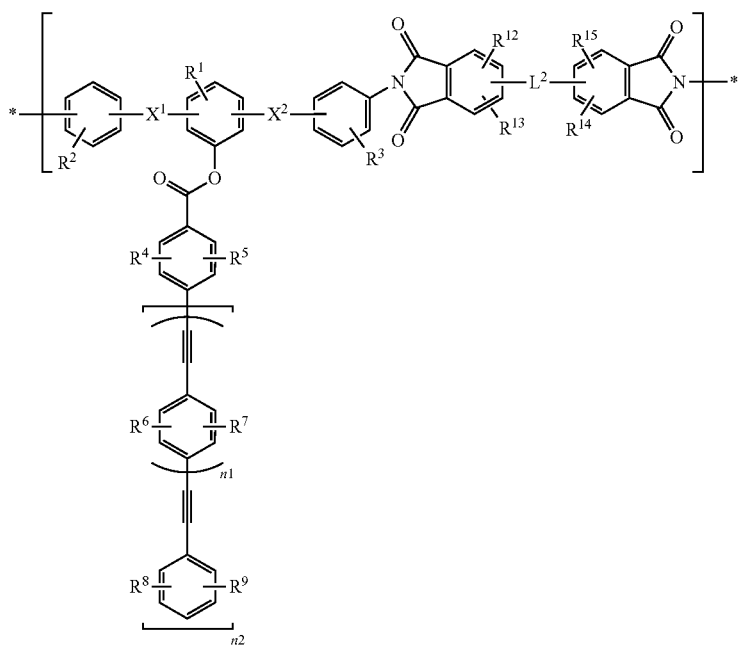

Chemical Formula 15

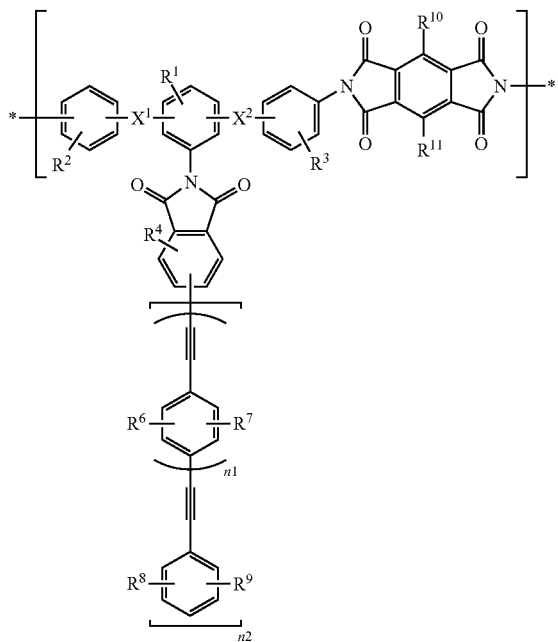

Chemical Formula 16

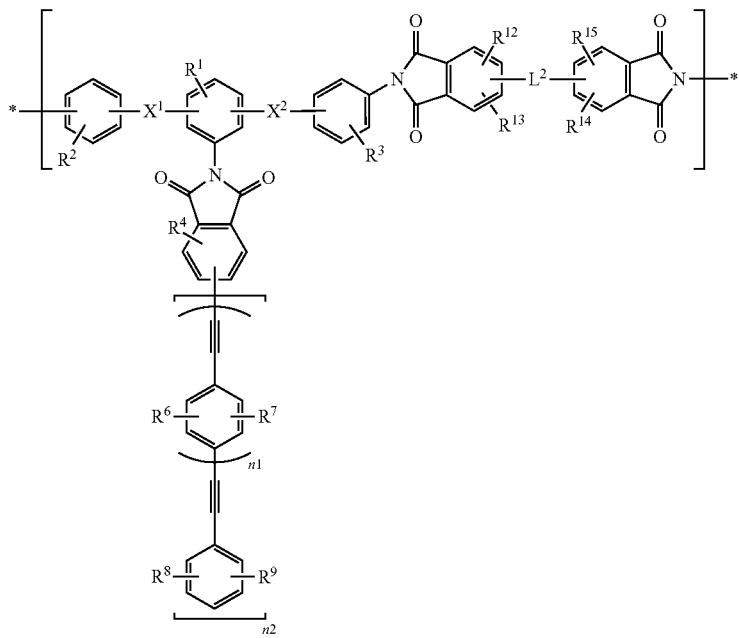

In Chemical Formulae 11 to 16, $X^1$, $X^2$, $R^1$ to $R^9$, n1, and n2 are the same as described above, $R^{12}$ to $R^{15}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, and

* indicates a binding site to an adjacent atom.

The polyimide may be obtained by copolymerizing at least one other monomer in addition to the monomer represented by Chemical Formula 1, and may further include at least one structural unit derived from the at least one other monomer. The other monomer may have a reaction site that is capable of reacting with the anhydride during polymerization to form a polyimide, for example a diamine compound.

For example, the polymer may further include a second structural unit represented by Chemical Formula 17 or 18 in addition to the first structural unit represented by Chemical Formula 10.

Chemical Formula 17

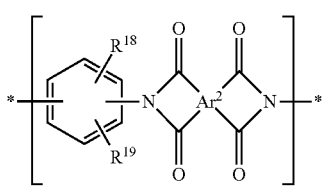

Chemical Formula 18

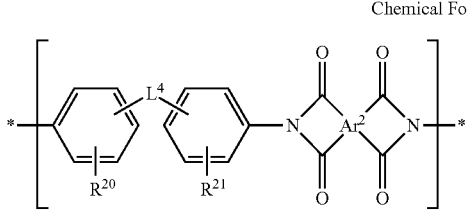

In Chemical Formula 17 or 18, $Ar^2$ is a substituted or unsubstituted C6 to C30 arylene group, $L^4$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, $R^{18}$ to $R^{21}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

The second structural unit represented by Chemical Formula 17 may be, for example represented by Chemical Formula 17a or 17b.

Chemical Formula 17a

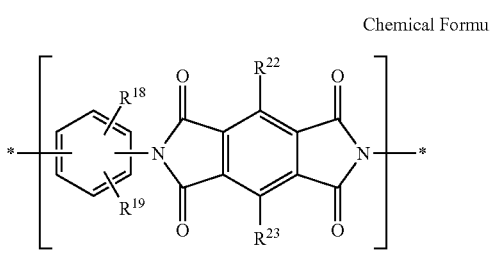

Chemical Formula 17b

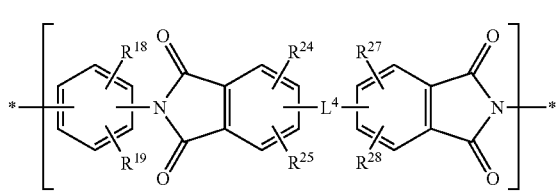

In Chemical Formula 17a or 17b, $L^4$, $R^{18}$, and $R^{19}$ are the same as described above, $R^{22}$ to $R^{27}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

The second structural unit represented by Chemical Formula 18 may be, for example represented by Chemical Formula 18a or 18b.

Chemical Formula 18a

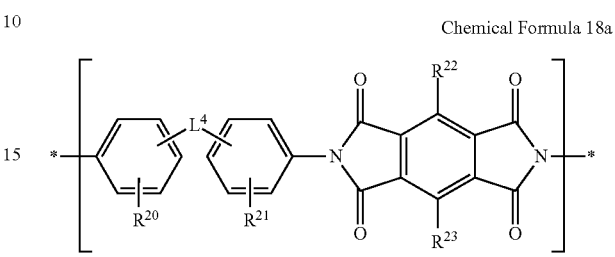

Chemical Formula 18b

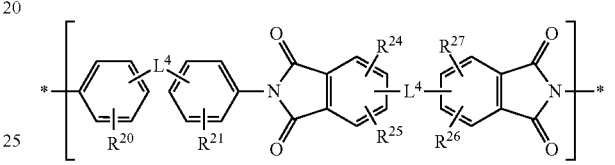

In Chemical Formulae 18a or 18b, $L^4$, $R^{20}$ to $R^{27}$, and * are the same as described above.

When the polyimide includes the first structural unit and the second structural unit, the first structural unit and the second structural unit may be included in a mole ratio of about 0.1:99.9 to about 99.9 to 0.1. While not wishing to be bound by theory, it is understood that within the above ranges, flexibility may be fortified while desirable optical properties may be attained, and thus, the polyimide may be readily transformed into a film. Within the above ranges, the first and second structural units may be, for example, included in a mole ratio of about 0.1:99.9 to about 10.0:90.0, for example about 0.5:99.5 to about 10:90, for example about 1:99 to about 10:99.

The polymer may be, for example prepared in a form of a film, and thus, may be used as a polymer film. The polymer film may be, for example transparent, and thus, may be applicable to any device that needs transparency. The polymer film may be used for various applications, for example a substrate, a protective film, a compensation film, an optical film, a dielectric layer, an insulation layer, an adhesive layer, and the like.

Hereinafter, a compensation film according to an embodiment is described.

A compensation film according to an embodiment includes the polymer.

That is, a compensation film according to an embodiment may include a first polymer that is a homopolymer of the monomer represented by Chemical Formula 1 or a copolymer with at least one other monomer.

For example, the compensation film may include a first polymer having the first structural unit represented by Chemical Formula 5.

In another example, the compensation film may include a first polymer having the first structural unit represented by any one of Chemical Formulae 6 to 8.

In another example, the compensation film may include a first polymer having the first structural unit represented by any one of Chemical Formulae 6a to 6d, 7a to 7d, 8a to 8d.

In another example, the compensation film may include a first polymer having a second structural unit that is different from the first structural unit, in addition to the first structural unit represented by Chemical Formula 5.

In another example, the compensation film may include a first polymer having the first structural unit represented by Chemical Formula 5 and the second structural unit represented by Chemical Formula 9.

In another example, the compensation film may include a first polymer having the first structural unit represented by Chemical Formula 10.

In another example, the compensation film may include a first polymer having the first structural unit represented by any one of Chemical Formulae 11 to 16.

In another example, the compensation film may include a first polymer having a second structural unit that is different from the first structural unit, in addition to the first structural unit represented by Chemical Formula 10.

In another example, the compensation film may include a first polymer having the first structural unit represented by Chemical Formula 10 and the second structural unit represented by Chemical Formula 17 or 18.

In another example, the compensation film may include a first polymer having the first structural unit represented by Chemical Formula 10 and the second structural unit represented by Chemical Formula 17a, 17b, 18a, or 18b.

The compensation film may further include at least one second polymer in addition to the first polymer. By including the second polymer, the optical physical characteristics of the compensation film may further be fortified.

The second polymer may be any polymer which fortifies a function of the compensation film, and is not particularly limited.

For example, the second polymer may have, for example a structural unit represented by Chemical Formula 17.

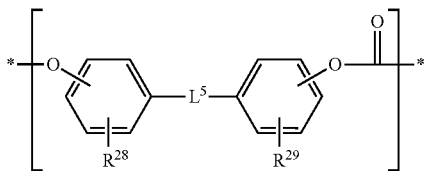

Chemical Formula 17

In Chemical Formula 17, $L^5$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, $R^{28}$ and $R^{29}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

For example, the second polymer may have a polyimide main chain.

The first polymer and the second polymer may be included, for example in a mole ratio of about 1:9 to about 9:1, for example about 1:9 to about 2:8, about 1:9 to about 3:7, or about 1:9 to about 5:5. While not wishing to be bound by theory, it is understood that within the above ranges, flexibility may be fortified while desirable optical properties may be attained and thus, the first and second polymers may be readily transformed into a film.

The compensation film may be, for example elongated in a uniaxial or biaxial direction. For example, the compensation film may be elongated in a uniaxial direction.

As described above, the compensation film may have a predetermined retardation by changing a refractive index and light absorption characteristics depending on a wavelength.

Retardation (R) of the compensation film may be expressed as an in-plane phase retardation ($R_0$) and a thickness direction retardation ($R_{th}$).

The in-plane phase retardation ($R_0$) of the compensation film is a retardation generated in an in-plane direction of the compensation film, which is represented by $R_0=(n_x-n_y)d$. The thickness direction retardation ($R_{th}$) of the compensation film is a retardation of the compensation film generated in a thickness direction and represented by $R_{th}=\{[(n_x+n_y)/2]-n_z\}d$. Herein, $n_x$ is a refractive index in a direction having a highest refractive index in a plane of a compensation film (hereinafter referred to as 'slow axis'), $n_y$ is a refractive index in a direction having a lowest refractive index in a plane of the compensation film (hereinafter referred to as 'fast axis'), $n_z$ is a refractive index in a direction perpendicular to the slow axis and the fast axis of a compensation film, and d is a thickness of a compensation film.

The compensation film may have an in-plane retardation and a thickness direction retardation within a predetermined range by changing the $n_x$, $n_y$, $n_z$, and/or the thickness (d).

The compensation film may have the same or different retardation depending on a wavelength.

For example, the compensation film may have a forward wavelength dispersion retardation, wherein a retardation of light at a shorter wavelength is larger than a retardation of light at a longer wavelength. When a 550 nanometer (nm) wavelength is a reference wavelength, for example retardations (R) in 450 nm, 550 nm, and 650 nm wavelengths of the compensation film may satisfy Relationship Equation 1 or 2.

$R(450\ nm) \geq R(550\ nm) > R(650\ nm)$  Relationship Equation 1

$R(450\ nm) > R(550\ nm) \geq R(650\ nm)$  Relationship Equation 2

For example, the compensation film may have a flat dispersion retardation where a retardation of light at a longer wavelength and a retardation of light at a shorter wavelength are substantially equivalent. For example retardations (R) in 450 nm, 550 nm, and 650 nm wavelengths of the compensation film may satisfy Relationship Equation 3.

$R(450\ nm) = R(550\ nm) = R(650\ nm)$  Relationship Equation 3

For example, the compensation film may have a reverse wavelength dispersion retardation where a retardation of light at a longer wavelength is larger than a retardation of light at a shorter wavelength. For example retardations (R) in 450 nm, 550 nm, and 650 nm wavelengths of the compensation film may satisfy Relationship Equation 4 or 5.

$R(450\ nm) \leq R(550\ nm) < R(650\ nm)$  Relationship Equation 4

$R(450\ nm) < R(550\ nm) \leq R(650\ nm)$  Relationship Equation 5

In Relationship Equations 1 to 5,

R (450 nm) is in-plane phase retardation or thickness direction retardation at a 450 nm wavelength of the compensation film, R (550 nm) is in-plane phase retardation or thickness direction retardation at a 550 nm wavelength of the compensation film, and R (650 nm) is in-plane phase retardation or thickness direction retardation at a 650 nm wavelength of the compensation film.

The compensation film may be varied to have desirable retardation depending on a wavelength.

The compensation film may have a relatively low thickness due to high birefringence. The compensation film may have, for example a thickness of about 3 micrometers (μm) to about 200 μm, for example about 5 μm to about 150 μm, or about 5 μm to about 100 μm.

The compensation film includes a substantially transparent polymer, and thus, may be used as a substrate, so a separate substrate under the compensation film may be omitted. Thereby, a thickness of the compensation film may be further reduced. Accordingly, the compensation film may be may be effectively applied in a flexible display device such as a foldable display device or a bendable display device, and may improve optical properties and display characteristics of the device.

The compensation film may be manufactured by a method including, for example preparing monomers, polymerizing the monomers to prepare a polymer, preparing the polymer in a form of a film, and elongating the film.

The compensation film may be, for example elongated at an elongation rate of about 110% to about 1,000% at a temperature of about 50° C. to about 500° C. The elongation rate refers to a length ratio of after the elongation to before the elongation of the compensation film, and reflects the elongation extent of the compensation film after uniaxial elongation.

The compensation film may be used alone or together with another compensation film.

The compensation film may be used with a polarizer which may be used as an optical film to prevent reflection of external light of a display device. The optical film may be, for example an antireflective film, but is not limited thereto.

Figure 2:
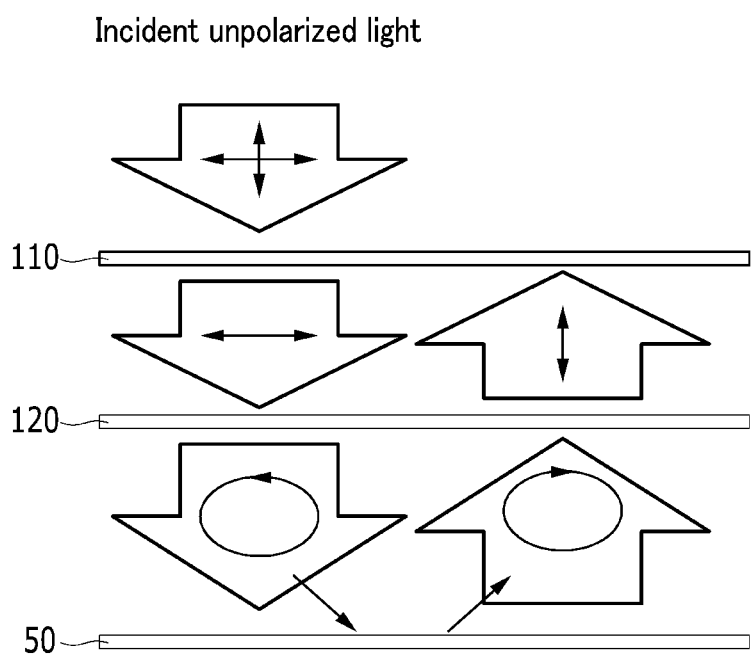
FIG. 2 is a schematic view showing the external light anti-reflection principle of an optical film.
Figure 3:
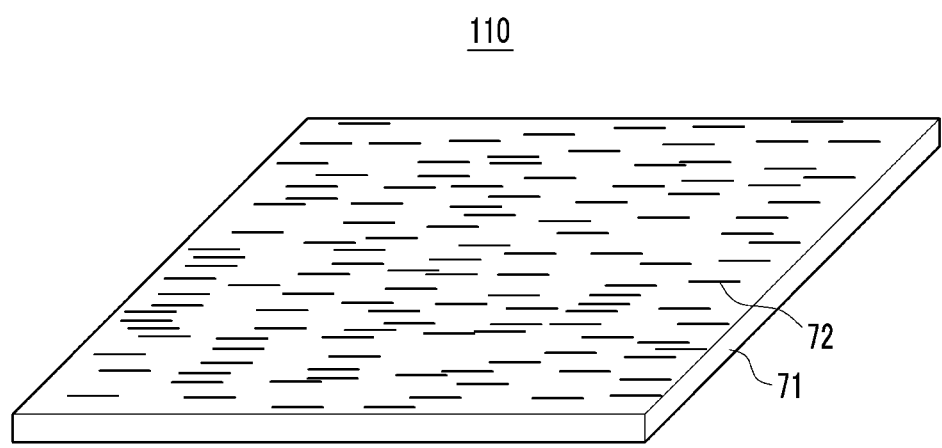
FIG. 3 is a schematic view of an example of a polarizing film.

FIG. 1 is a schematic cross-sectional view showing an optical film according to an embodiment, FIG. 2 is a schematic view showing the external light anti-reflection principle of an optical film, and FIG. 3 is a schematic view of an example of a polarizing film.

Referring to FIG. 1, an optical film 100 according to an embodiment includes a polarizer 110 and a compensation film 120. The compensation film 120 may allow circularly polarized light passed through the polarizer 110 to generate retardation, and may influence reflection and/or absorption of light.

For example, the optical film 100 may be mounted on one side or both sides of the display device, and particularly, may prevent light from flowing into the display part of the display device from the outside (hereinafter referred to as 'external light') from being reflected. Accordingly, the optical film 100 may prevent the visibility deterioration caused by the external light reflection.

FIG. 2 is a schematic view showing the external light anti-reflection principle of an optical film.

Referring to FIG. 2, while the incident unpolarized light having entered from the outside is passed through the polarizer 110, and the polarized light is shifted into circularly polarized light by passing through the compensation film 120, only a first polarized perpendicular component, which is one polarized perpendicular component of two polarized perpendicular components, is transmitted. While the circularly polarized light is reflected in a display panel 50 including a substrate, an electrode, and so on, changing the circular polarization direction, and while the circularly polarized light is passed through the compensation film 120 again, only a second polarized perpendicular component, which is the other polarized perpendicular component of the two polarized perpendicular components, may be transmitted. As the second polarized perpendicular component is not passed through the polarizer 110, and since light does not exit to the outside, effects of preventing the external light reflection may be provided.

The polarizer 110 may be, for example a polarizing plate or a polarization film.

Referring to FIG. 3, the polarizer 110 may be a self-integrated polarizing film made of, for example a melt blend of a polymer 71 and a dichroic dye 72.

The polymer 71 may be, for example a hydrophobic polymer, for example a polyolefin such as polyethylene (PE), polypropylene (PP), and a copolymer thereof; a polyamide such as nylon and aromatic polyamide; a polyester such as polyethylene terephthalate (PET), polyethylene terephthalate glycol (PETG), and polyethylene naphthalate (PEN); a polyacryl such as polymethyl(meth)acrylate; a polystyrene such as polystyrene (PS) and an acrylonitrile-styrene copolymer; a polycarbonate; a vinyl chloride polymer; a polyimide; a sulfone polymer; a polyethersulfone; a polyether-etherketone; a polyphenylene sulfide; a vinyl alcohol polymer; a vinylidene chloride polymer; a vinyl butyral polymer; an allylate polymer; a polyoxymethylene; epoxy, a copolymer thereof, or a combination thereof.

In an embodiment, the polymer 71 may be, for example a polyolefin, a polyamide, a polyester, a polyacrylic, a polystyrene, a copolymer thereof, or a combination thereof, and may be, for example polyethylene (PE), polypropylene (PP), polyethylene terephthalate (PET), polyethylene terephthalate glycol (PETG), polyethylene naphthalate (PEN), nylon, a copolymer thereof, or a combination thereof.

In an embodiment, the polymer 71 may be polyolefin. The polyolefin may be, for example a mixture of two or more selected from polyethylene (PE), polypropylene (PP), a copolymer of polyethylene and polypropylene (PE-PP), for example a mixture of polypropylene (PP) and a polyethylene-polypropylene copolymer (PE-PP).

The polymer 71 may have a transmittance of greater than or equal to about 85% in a wavelength region of about 400 nm to about 780 nm. The polymer 71 may be elongated in a uniaxial direction. The uniaxial direction may be the same as a length direction of the dichroic dye 72, which will be described later.

The dichroic dye 72 may be dispersed in the polymer 71, and may be aligned in the elongation direction of the polymer 71. The dichroic dye 72 transmits one perpendicular polarization component out of two perpendicular polarization components in a predetermined wavelength region.

The dichroic dye 72 may be included in an amount of about 0.01 to about 5 parts by weight based on 100 parts by weight of the polymer 71. While not wishing to be bound by theory, it is understood that within the above range, sufficient polarization characteristics may be obtained without deteriorating transmittance of a polarization film. Within the above range, the dichroic dye may be included in an amount of about 0.05 to about 1 part by weight based on 100 parts by weight of the polymer 71.

The polarizer 110 may have a relatively low thickness of less than or equal to about 100 μm, for example, for example about 30 μm to about 95 μm. While not wishing to be bound by theory, it is understood that when the polarizer 110 has a thickness with the above range, thickness of the polarizer 110 is relatively lower than that of a polyvinyl alcohol polarizing plate requiring a protective layer such as triacetyl cellulose (TAC), and thus, a thin display device may be realized.

The compensation film 120 is the same as described above.

The optical film 100 may further include a correction layer (not shown) positioned on one side of the compensation film 120. The correction layer may be, for example, a color shift resistant layer, but is not limited thereto.

The optical film 100 may further include a light blocking layer (not shown) extended along the edge. The light blocking layer may be formed in a strip along the circumference of the optical film 100, and for example, may be positioned between the polarizer 110 and the compensation film 120. The light blocking layer may include an opaque material, for example, a black material. For example, the light blocking layer may be made of a black ink.

The optical film 100 may be applied to various display devices.

A display device according to an embodiment includes a display panel and an optical film positioned on one side of the display panel. The display panel may be a liquid crystal panel or organic light emitting panel, but is not limited thereto.

Hereinafter, an organic light emitting device is described as an example of a display device.

Figure 4:
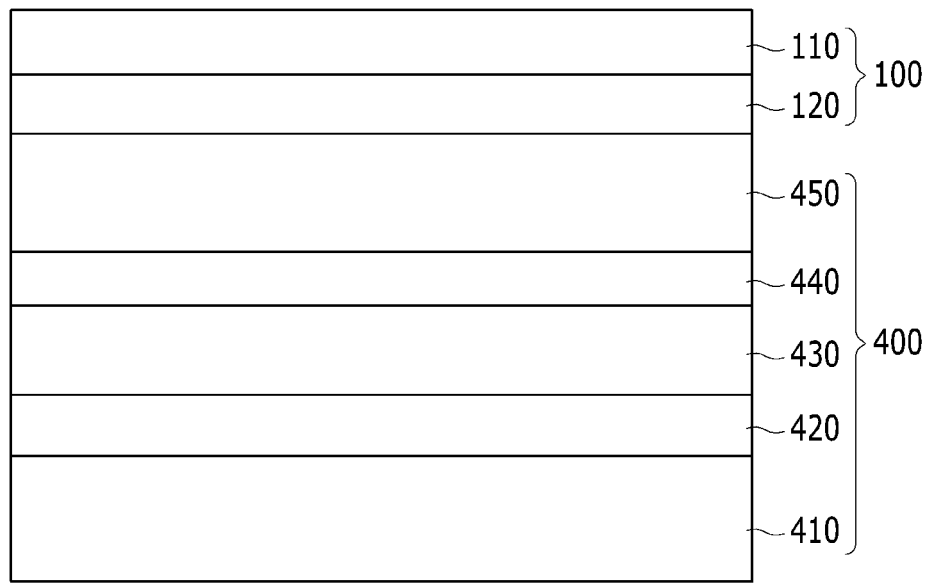
FIG. 4 is a schematic cross-sectional view showing an organic light emitting device according to an embodiment.

FIG. 4 is a schematic cross-sectional view showing an organic light emitting device according to an embodiment.

Referring to FIG. 4, the organic light emitting device according to an embodiment includes an organic light emitting panel 400 and an optical film 100 positioned on one side of the organic light emitting diode panel 400.

The organic light emitting diode panel 400 may include a base substrate 410, a lower electrode 420, an organic emission layer 430, an upper electrode 440, and an encapsulation substrate 450.

The base substrate 410 may be made of glass or plastic.

At least one of the lower electrode 420 and the upper electrode 440 may be an anode, and the other one may be a cathode. The anode is an electrode injected with holes, and may be made of a transparent conductive material having a high work function to transmit the emitted light to the outside, for example, ITO or IZO. The cathode is an electrode injected with electrons, and may be made of a conductive material having a low work function without affecting the organic material, and may be selected from, for example, aluminum (Al), calcium (Ca), and barium (Ba).

The organic emission layer 430 includes an organic material which may emit light when a voltage to the lower electrode 420 and the upper electrode 440 is applied.

An auxiliary layer (not shown) may be further provided between the lower electrode 420 and the organic emission layer 430 and between the upper electrode 440 and the organic emission layer 430. The auxiliary layer is used to balance electrons and holes, and may include a hole transport layer, a hole injection layer (HIL), an electron injection layer (EIL), and an electron transporting layer.

The encapsulation substrate 450 may be made of glass, metal, or a polymer, and may seal the lower electrode 420, the organic emission layer 430, and the upper electrode 440 to prevent moisture and/or oxygen inflow from the outside.

The optical film 100 may be disposed on the light-emitting side. For example, in a bottom emission structure emitting light at the side of the base substrate 410, the optical film 100 may be disposed on the exterior side of the base substrate 410. On the other hand, in a top emission structure emitting light at the side of the encapsulation substrate 450, the optical film 100 may be disposed on the exterior side of the encapsulation substrate 450.

The optical film 100 includes the self-integrated polarizer 110 and the self-integrated compensation film 120. The polarizer 110 and the compensation film 120 are respectively the same as described above, and may prevent a display device from having visibility deterioration caused by light inflowing from the outside after passing the polarizer 110 and being reflected by a metal such as an electrode and the like in the organic light emitting panel 400. Accordingly, display characteristics of the organic light emitting device may be improved.

Hereinafter, a liquid crystal display (LCD) is described as an example of the display device.

Figure 5:
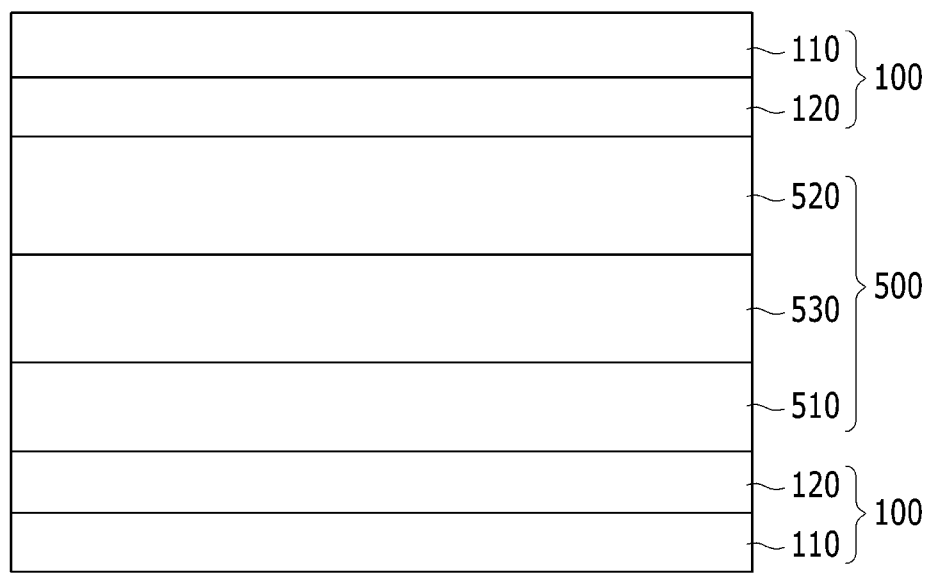
FIG. 5 is a schematic cross-sectional view showing a liquid crystal display according to an embodiment.

FIG. 5 is a schematic cross-sectional view showing a liquid crystal display according to an embodiment.

Referring to FIG. 5, the liquid crystal display (LCD) according to an embodiment includes a liquid crystal display panel 500, and an optical film 100 positioned on one side or both sides of the liquid crystal panel 500.

The liquid crystal panel 500 may be a twist nematic (TN) mode panel, a vertical alignment (PVA) mode panel, an in-plane switching (IPS) mode panel, an optically compensated bend (OCB) mode panel, or the like.

The liquid crystal panel 500 may include a first display panel 510, a second display panel 520, and a liquid crystal layer 530 interposed between the first display panel 510 and the second display panel 520.

The first display panel 510 may include, for example, a thin film transistor (not shown) formed on a substrate (not shown) and a first electric field generating electrode (not shown) connected to the same, and the second display panel 520 may include, for example, a color filter (not shown) formed on a substrate (not shown) and a second electric field generating electrode (not shown). However, it is not limited thereto, and the color filter may be included in the first display panel 510, while the first electric field generating electrode and the second electric field generating electrode may be disposed on the first display panel 510 together therewith.

The liquid crystal layer 530 may include a plurality of liquid crystal molecules. The liquid crystal molecules may have positive or negative dielectric anisotropy. When the liquid crystal molecules have positive dielectric anisotropy, the major axes thereof may be aligned substantially parallel to the surface of the first display panel 510 and the second display panel 520 when an electric field is not applied, and the major axes may be aligned substantially perpendicular to the surface of the first display panel 510 and second display panel 520 when an electric field is not applied. On the other hand, when the liquid crystal molecules have negative dielectric anisotropy, the major axes may be aligned substantially perpendicular to the surface of the first display panel 510 and the second display panel 520 when an electric field is not applied, and the major axes may be aligned substantially parallel to the surface of the first display panel 510 and the second display panel 520 when an electric field is applied.

The optical film 100 may be disposed on the outside of the liquid crystal panel 500. Although the optical film 100 is shown to be provided on both the lower part and the upper part of the liquid crystal panel 500 in the drawing, it is not limited thereto, and it may be formed on only one of the lower part and the upper part of the liquid crystal panel 500.

Hereinafter, the present disclosure is illustrated in more detail with reference to examples. However, these examples are exemplary, and the present disclosure is not limited thereto.

EXAMPLES

Synthesis of Monomer

Synthesis Example 1

Step 1

Reaction Scheme 1

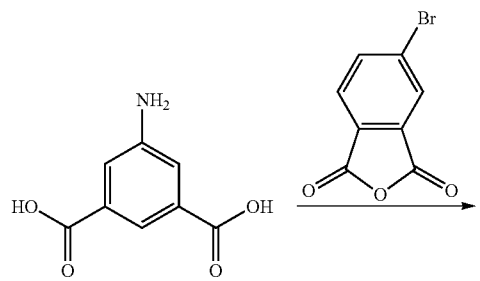

5-aminoisophthalic acid (molecular weight (mw)=181.15 grams per mole (g/mol), number of moles (v)=0.6 moles (mol), mass (m)=108.7 grams, gr) is placed in 1 liter (L) of dimethyl acetamide (DMAC) and dissolved therein at 60° C. while stirred. Subsequently, 4-bromophthalic anhydride (mw=227.02 g/mol, v=0.6 mol, m=136.2 gr) is added to the solution, and the mixture is heated up to 100° C. and stirred for 1 hour. Then, acetic anhydride (mw=102.1 g/mol, v=0.9 mol, m=92 gr) and pyridine (mw=79.1 g/mol, v=0.9 mol, m=72 gr) are added to the solution, and the mixture is stirred for 2 hours to obtain a white solid precipitate. Subsequently, the resulting material is diluted with 1 L of isopropyl alcohol and cooled down to room temperature. The precipitate is filtered, cleaned with isopropyl alcohol, and dried under vacuum at 110° C. for 48 hours to obtain an intermediate I-1 (mw=390.2 g/mol, v=0.9 mol, m=234 gr). A yield is 100%.

$^1$H NMR (DMSO-$d_6$) 300 MHz, δ, parts per million (ppm): 7.93 (d, 1H, $J^{12}$=9 Hertz, Hz), 8.12 (dd, 1H, $J^{12}$=9 Hz, $J^{13}$=1.7 Hz), 8.21 (d, 1H, $J^{13}$=1.7 Hz), 8.29 (d, 2H, $J^{13}$=1.7 Hz), 8.51 (t, 1H, $J^{13}$=1.7 Hz).

Step 2

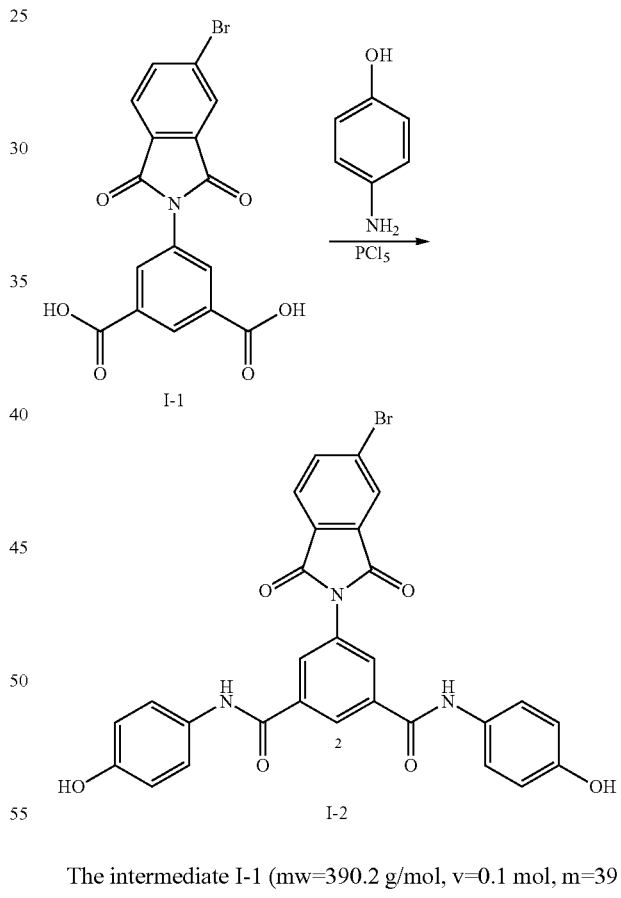

The intermediate I-1 (mw=390.2 g/mol, v=0.1 mol, m=39 gr), phosphorous pentachloride (PCl$_5$) (mw=208.2 g/mol, v=0.2 mol, m=42.7 gr), and one drop of pyridine are mixed and then, refluxed in 0.6 L of toluene for 2 hours. Subsequently, toluene and phosphorous oxychloride produced during the reaction are removed under a reduced pressure, and a yellow residue obtained therefrom is stirred and dissolved in 0.4 L of dimethyl acetamide (DMAC). Subsequently, 4-aminophenol (mw=109.3 g/mol, v=0.22 mol, m=24 gr) is added to the solution, and the mixture is heated up to 80° C. and further stirred for 2 hours. When the reaction is complete, the resultant is cooled down to room temperature, and 2 L of water is poured thereinto. Subsequently, a solid obtained therefrom is filtered and cleaned with water. The solid is filtered while boiled and cooled down in 0.7 L of isopropyl alcohol and filtered in 0.7 L of ethyl acetate while boiled and cooled down. Then, the solid is dried under vacuum at 100° C. for 24 hours to obtain a light beige solid, an intermediate I-2 (mw=572.8 g/mol, v=82.1 mmol, m=47 gr). A yield is 82.1%.

$^1$H NMR (DMSO-d$_6$) 300 MHz, δ, ppm: 6.77 (d, 4H, $J^{12}$=10 Hz), 7.57 (d, 4H, $J^{12}$=10 Hz), 7.95 (d, 1H, $J^{12}$=9 Hz), 8.14 (dd, 1H, $J^{12}$=9 Hz, $J^{13}$=1.7 Hz), 8.17 (d, 2H, $J^{13}$=1.7 Hz), 8.23 (d, 1H, $J^{13}$=1.7 Hz), 8.60 (s, 1H), 9.32 (br. s, 2H), 10.31 (s, 2H).

Step 3

Reaction Scheme 3

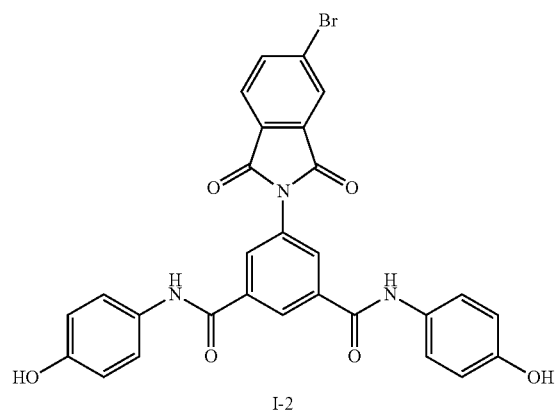

I-2

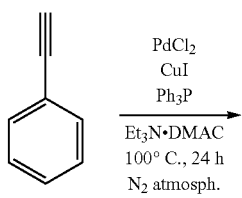

PdCl$_2$
CuI
Ph$_3$P
Et$_3$N·DMAC
100° C., 24 h
N$_2$ atmosph.

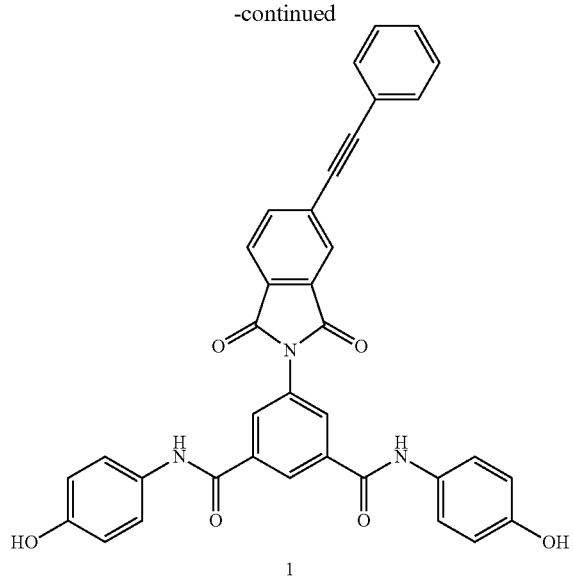

1

The intermediate I-2 (mw=572.8 g/mol, v=37.6 mmol, m=21.5 gr) is placed in a round-bottomed flask equipped with a nitrogen injection hole and a condenser and dissolved in a mixed solvent of 0.5 L of triethylamine (Et$_3$N) and dimethyl acetamide (DMAC) (1:1=volume to volume, v/v). The solution is purged with dry nitrogen gas for 1 hour, and phenylacetylene (mw=102.14 g/mol, v=45.1 mmol, m=4.6 gr), palladium (II) chloride, PdCl$_2$) (mw=177.33 g/mol, v=0.75 mmol, m=0.13 gr), copper (I) iodide (CuI) (mw=190.45 g/mol, v=1.5 mol, m=0.29 gr), and triphenylphosphine (Ph$_3$P) (mw=262.45 g/mol, v=3.0 mmol, m=0.79 gr) are added thereto. Subsequently, a resulting material obtained after being continuously supplied with nitrogen for 10 minutes is stirred under a nitrogen atmosphere at 100° C. for 24 hours. When the reaction is complete, a solvent is removed therefrom under a reduced pressure. Subsequently, the obtained solid is extracted with hot methanol, and its residue is consecutively treated with hot isopropyl alcohol and ethyl acetate. Then, a resulting material obtained therefrom is dried at 80° C. for 24 hours to obtain a light yellow solid, a compound 1 (mw=593.6 g/mol, v=27 mmol, m=16 gr). A yield is 71.8%.

$^1$H NMR (DMSO-d$_6$) 300 MHz, δ, ppm: 6.77 (d, 4H, $J^{12}$=10 Hz), 7.50 (m, 3H), 7.56 (d, 4H, $J^{12}$=10 Hz), 7.67 (m, 2H), 8.07 (s, 2H), 8.18 (m, 3H), 8.59 (s, 1H), 9.32 (s, 2H), 10.30 (s, 2H).

Synthesis of Polymer

Synthesis Example 2

Reaction Scheme 4

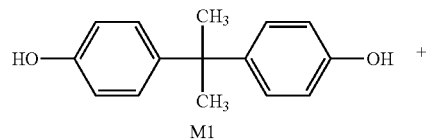

M1 +

-continued

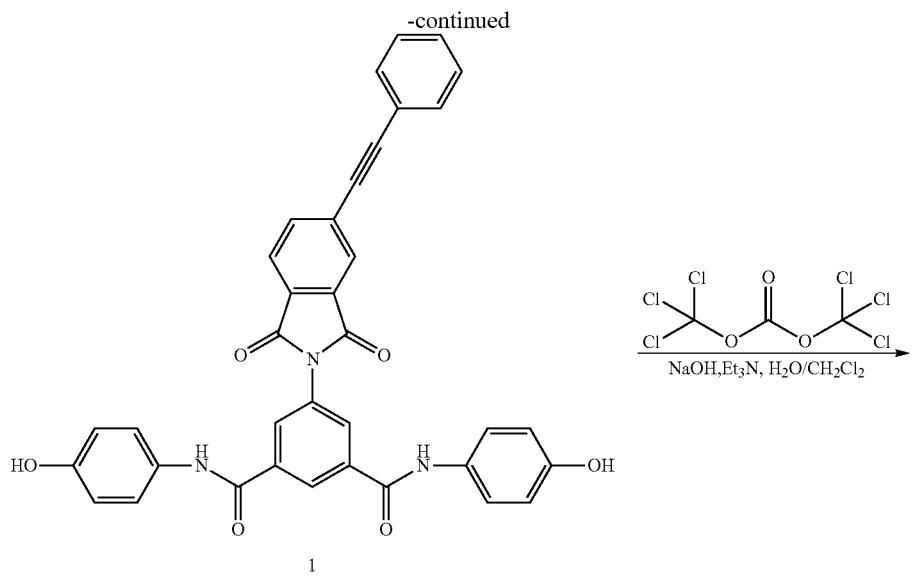

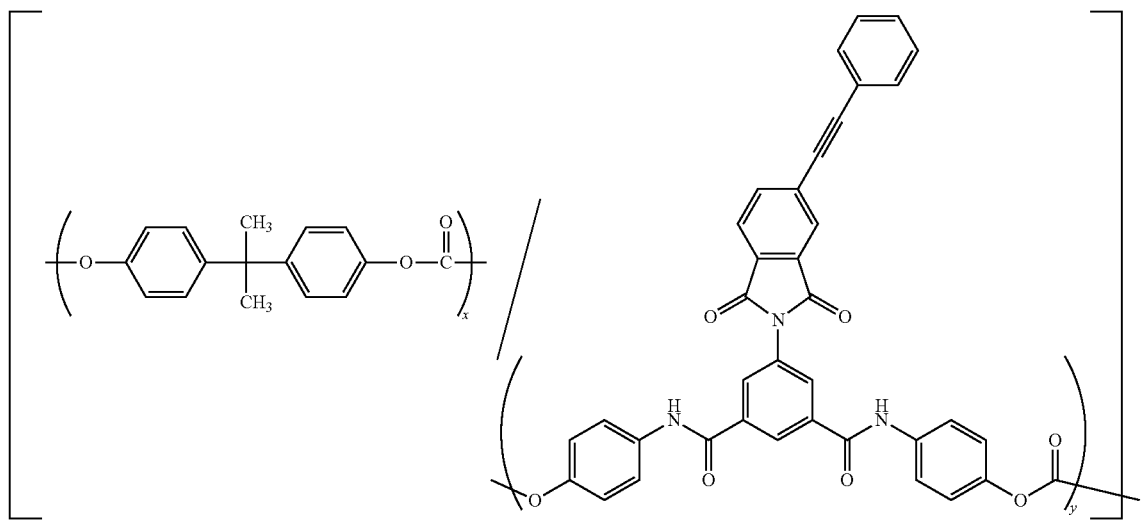

1.57 g of sodium hydroxide, 12 milliliters (mL) of water, 1.40 g of the compound M1, and 0.404 g of the compound 1 are placed in a 100 mL flask equipped with a mechanical stirrer. Herein, the compound M1 and the compound 1 are supplied in a mole ratio of 9:1. Subsequently, 0.909 g of triphosgene dissolved in 14 mL of dichloromethane is added thereto, and the mixture is stirred for 15 minutes. Then, 7.9 mg of triethylamine is added thereto, and the obtained mixture is stirred at room temperature for 90 minutes. When the reaction is complete, the resultant is diluted with water and dichloromethane, cleaned with a 1%-hydrochloric acid solution and water, re-precipitated with methanol, and then, vacuum-dried at 60° C. for 12 hours to obtain a polymer.

Synthesis Example 3

A polymer is obtained according to the same method as Synthesis Example 2 except for supplying the compound M1 and the compound 1 in a mole ratio of 9.9:0.1.

Synthesis Example 4

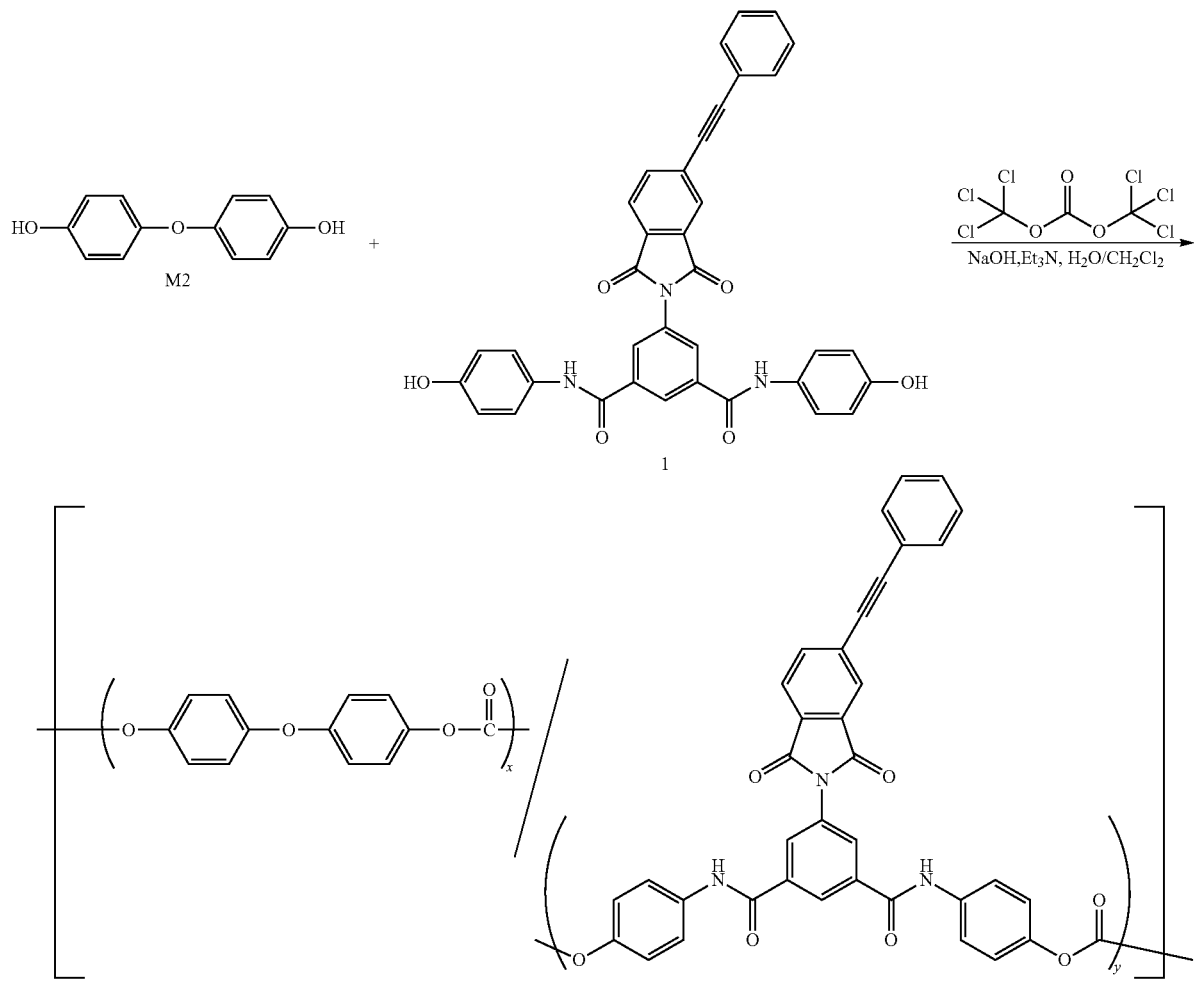

Reaction Scheme 5

Sodium hydroxide, 13 mL of water, 1.40 g of the compound M2, and 0.456 g of the compound 1 are placed in a 100 mL flask equipped with a mechanical stirrer. Herein, the compound M2 and the compound 1 are supplied in a mole ratio of 9:1. Subsequently, 1.03 g of triphosgene dissolved in 17 mL of dichloromethane is added thereto, and the mixture is stirred for 15 minutes. Then, 7.01 mg of triethylamine is added thereto, and the obtained mixture is stirred at room temperature for 90 minutes. When the reaction is complete, the resultant is diluted with water and dichloromethane, cleaned with 1%-hydrochloric acid and water, re-precipitated with methanol, and vacuum-dried at 60° C. for 12 hours to obtain 0.650 g of a polymer.

Manufacture of Compensation Film

Example 1

The polymer according to Synthesis Example 2 and a polymer ($\eta_{inh}$=1.45 grams per deciliter, g/dL) having a structural unit represented by Chemical Formula A in a mole ratio of 1:1 are dissolved in a mixed solvent of tetrahydrofuran and dioxane (1/1, v/v), manufacturing a polymer solution having a concentration of 20 percent by weight (wt %). Subsequently, the polymer solution is coated on a glass substrate and dried at 40° C. for 1 hour and at 80° C. for 1 hour, forming a compensation film. Then, the compensation film is detached from the glass substrate.

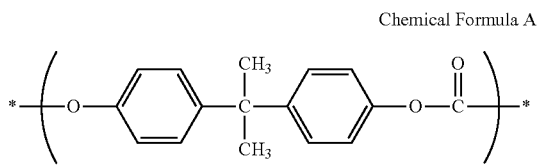

Chemical Formula A wherein in Chemical Formula A, * indicates a binding site to an adjacent atom.

Example 2

A compensation film is manufactured according to the same method as Example 1 except for using the polymer according to Synthesis Example 3 instead of the polymer according to Synthesis Example 2.

Evaluation 1

Light transmittance of the compensation films according to Examples 1 and 2 is evaluated.

The light transmittance is measured by using a KONICA MINOLTA Spectrophotometer CM-3600.

The results are shown in Table 1.

TABLE 1

|  | Light transmittance (%) |
|---|---|
| Example 1 | 81.2 |
| Example 2 | 83.5 |

The compensation films according to Examples 1 and 2 have satisfactory light transmittance of greater than or equal to about 80%.

Evaluation 2

In-plane phase retardations and thickness direction retardations of the compensation film according to Examples 1 and 2 are measured, and wavelength dispersion is evaluated therefrom.

The in-plane phase retardations and thickness direction retardations are measured using an Axoscan equipment (Axometrics, Inc.).

Wavelength dispersion of in-plane phase retardations are shown in Table 2.

TABLE 2

|  | $R_o$ (450 nm)/ $R_o$ (550 nm) | $R_o$ (650 nm)/ $R_o$ (550 nm) |
|---|---|---|
| Example 1 | 0.91 | 1.04 |
| Example 2 | 1.30 | 0.92 |

Wavelength dispersion of thickness direction retardations is shown in Table 3.

TABLE 3

|  | $R_{th}$ (450 nm)/ $R_{th}$ (550 nm) | $R_{th}$ (650 nm)/ $R_{th}$ (550 nm) |
|---|---|---|
| Example 1 | 0.82 | 1.13 |
| Example 2 | 1.07 | 0.73 |

Referring to Tables 2 and 3, the compensation films according to Examples 1 and 2 have a forward wavelength dispersion retardation where a retardation of light at a shorter wavelength is larger than a retardation of light at a longer wavelength, or a reverse wavelength dispersion retardation where a retardation of light at a longer wavelength is larger than a retardation of light at a shorter wavelength. From the results, it is determined that compensation films having desirable retardations and wavelength dispersion may be realized by controlling various factors such as a nature and a content ratio of a polymer.

While this disclosure has been described in connection with what is presently considered to be practical exemplary embodiments, it is to be understood that the disclosure is not limited to the present embodiments, but, on the contrary, is intended to cover various modifications and equivalent arrangements included within the spirit and scope of the appended claims.

What is claimed is:

1. A monomer represented by Chemical Formula 1:

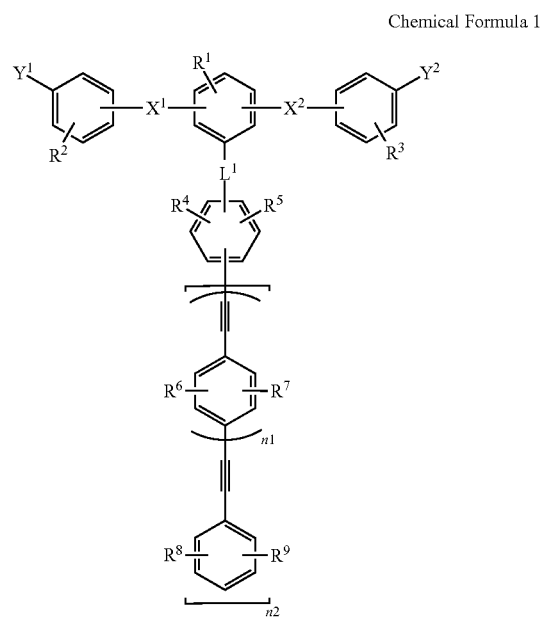

Chemical Formula 1 wherein in Chemical Formula 1, $X^1$, $X^2$, and $L^1$ are each independently O, C(=O), C(=O)O, or C(=O)$NR^a$, $Y^1$ and $Y^2$ are each independently OH or $NH_2$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, and n2 is 1 or 2.

2. The monomer of claim 1, wherein the monomer is represented by any one of Chemical Formulae 2 to 4:

Chemical Formula 2

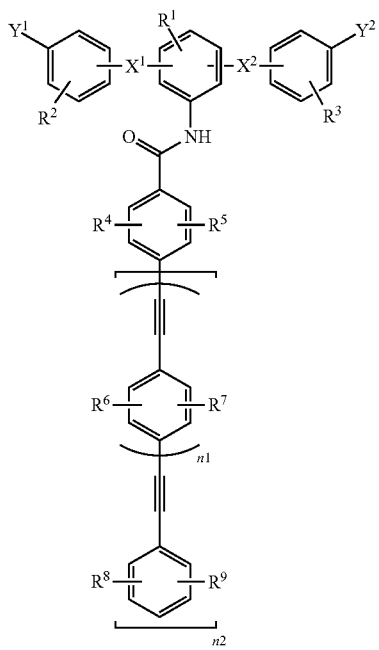

Chemical Formula 3

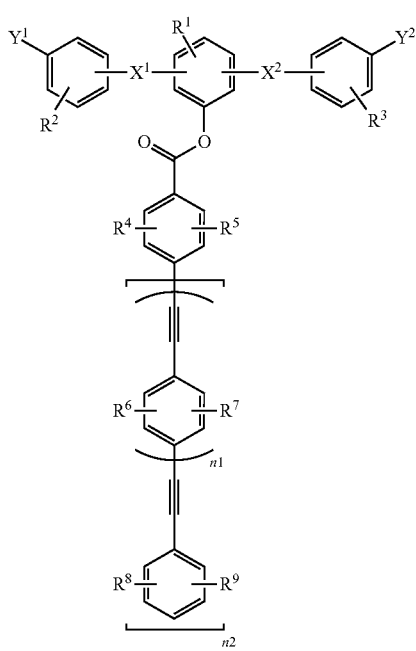

Chemical Formula 4

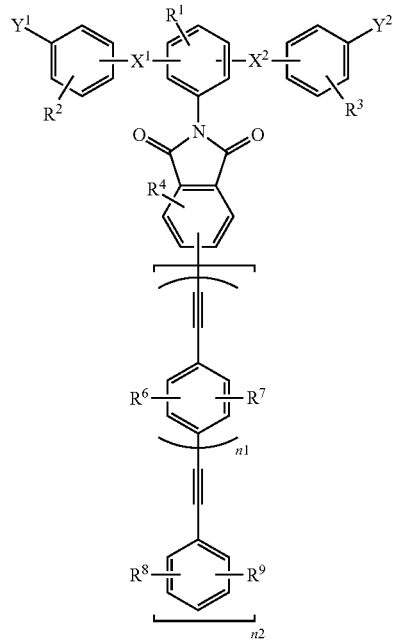

wherein in Chemical Formulae 2 to 4, $X^1$ and $X^2$ are each independently O, C(=O), C(=O)O, or C(=O)NR$^a$, $Y^1$ and $Y^2$ are each independently OH or NH$_2$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, n1 is an integer ranging from 0 to 3, and n2 is 1 or 2.

3. The monomer of claim 2, wherein the monomer represented by Chemical Formula 2 is represented by any one of Chemical Formulae 2a to 2d:

Chemical Formula 2a
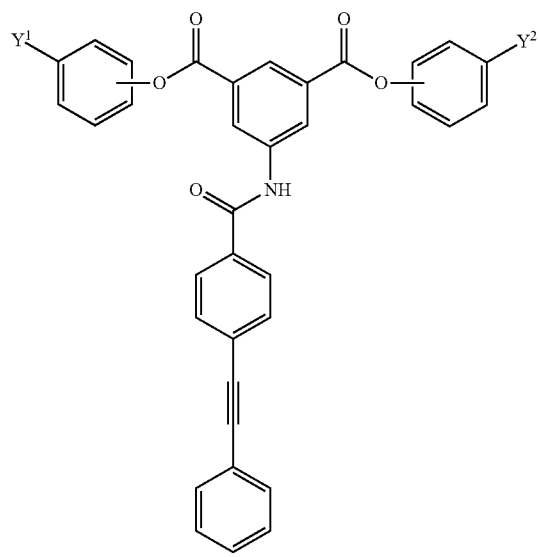
Chemical Formula 2b
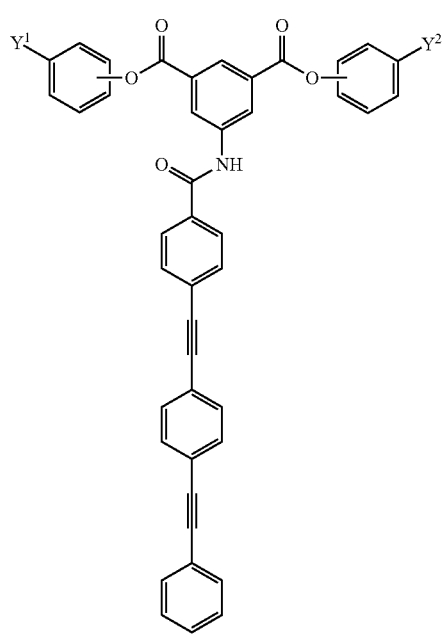
Chemical Formula 2c
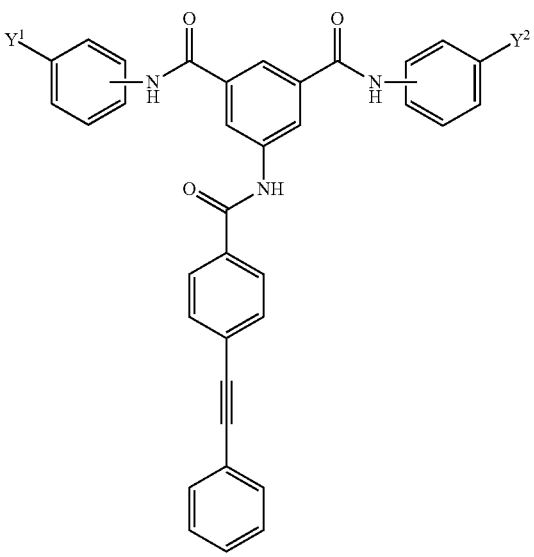
Chemical Formula 2d
wherein in Chemical Formulae 2a to 2d,
Y$^1$ and Y$^2$ are each independently OH or NH$_2$.
4. The monomer of claim 2, wherein the monomer represented by Chemical Formula 3 is represented by any one of Chemical Formulae 3a to 3d:

Chemical Formula 3a
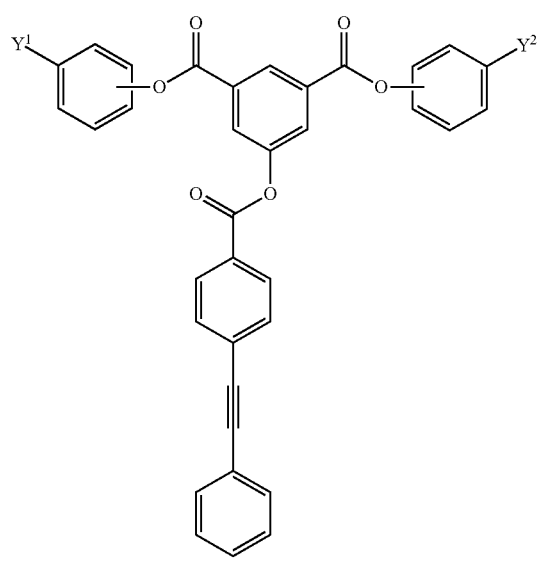
Chemical Formula 3c
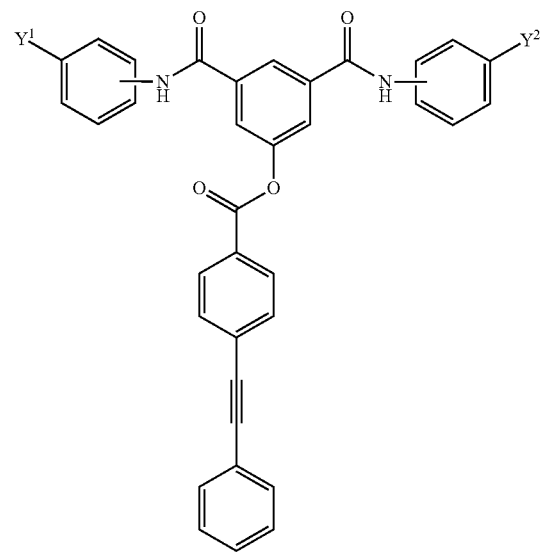
Chemical Formula 3b
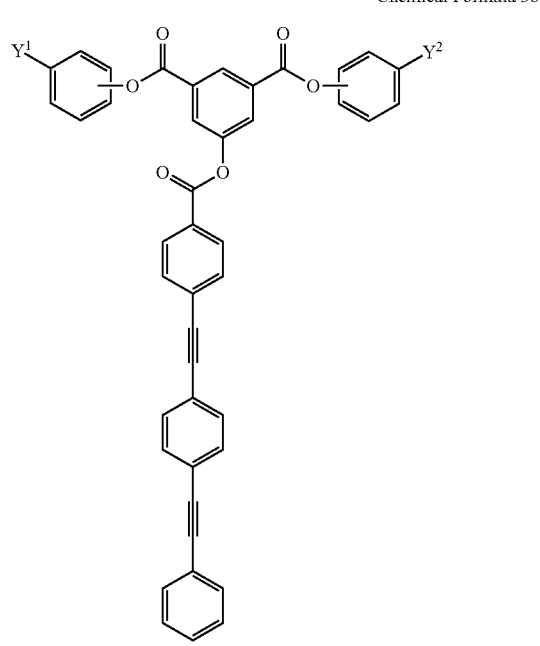
Chemical Formula 3d
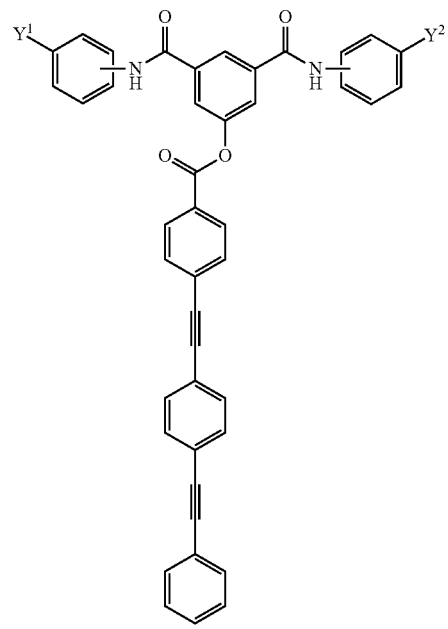
wherein in Chemical Formulae 3a to 3d,
Y$^1$ and Y$^2$ are each independently OH or NH$_2$.
5. The monomer of claim 2, wherein the monomer represented by Chemical Formula 4 is represented by any one of Chemical Formulae 4a to 4d:

Chemical Formula 4a

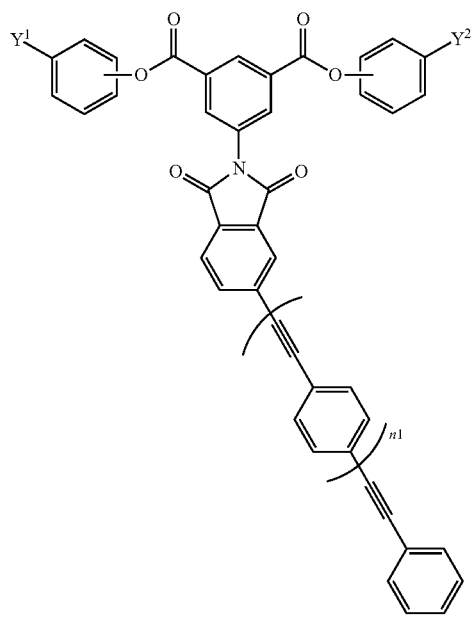

Chemical Formula 4c

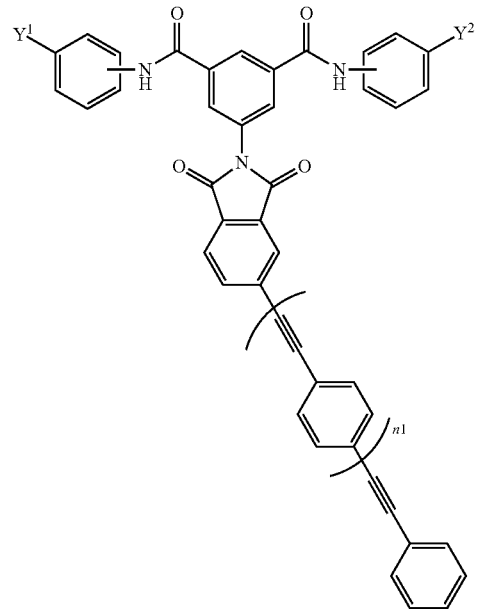

Chemical Formula 4d

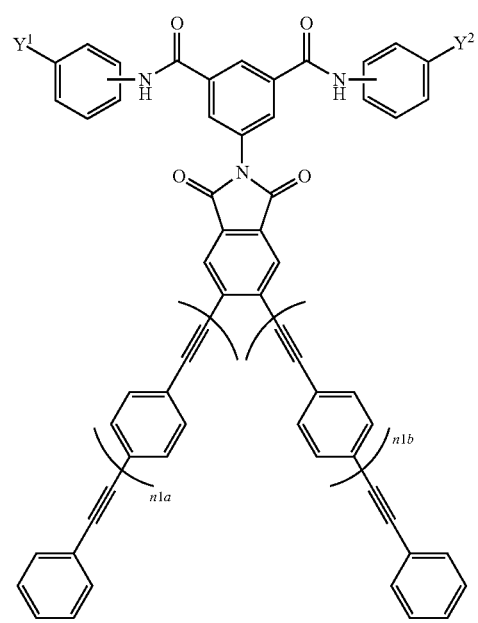

Chemical Formula 4b

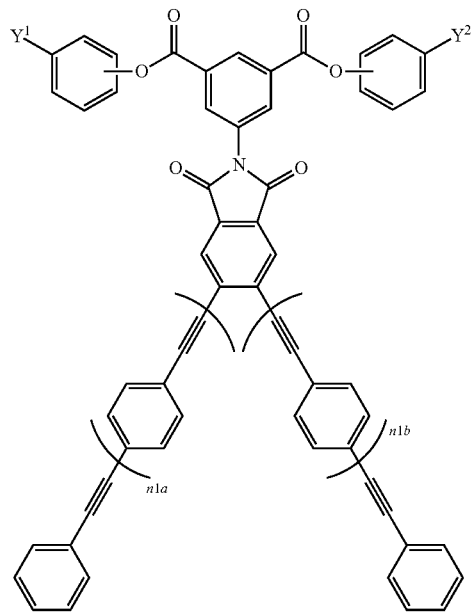

wherein in Chemical Formulae 4a to 4d, $Y^1$ and $Y^2$ are each independently OH or $NH_2$, and n1, n1a, and n1b are each independently an integer ranging from 0 to 3.

6. A polymer having a first structural unit derived from the monomer of claim 1.

7. The polymer of claim 6, wherein the first structural unit is a product of a reaction of the monomer and a carbonate compound or a product of a reaction of the monomer and an anhydride compound.

8. The polymer of claim 7, wherein the first structural unit is represented by Chemical Formula 5

Chemical Formula 5

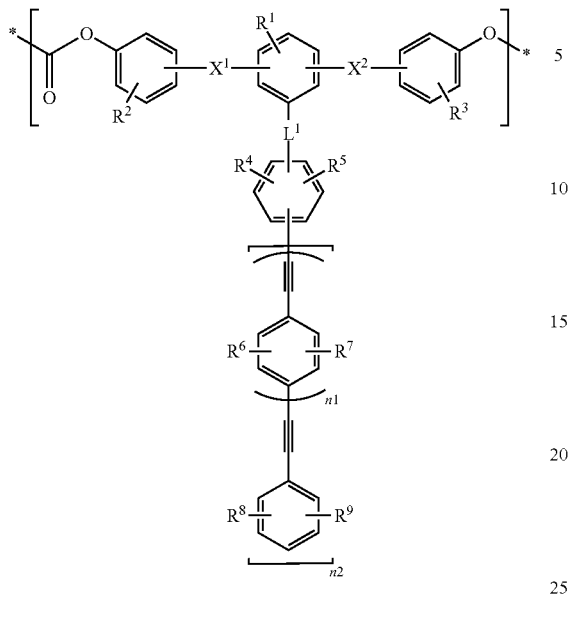

Chemical Formula 6

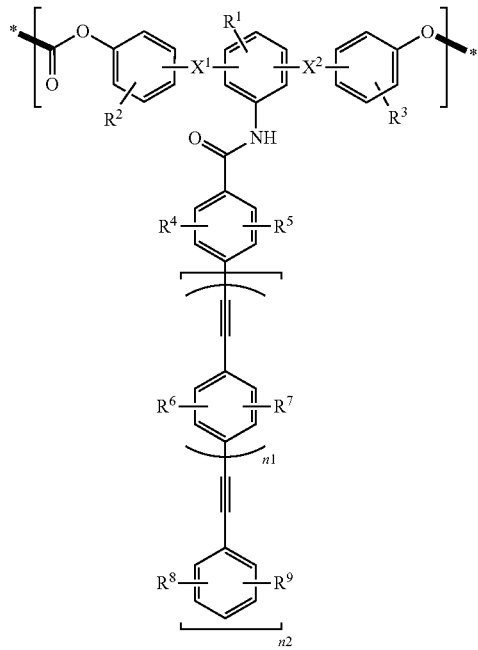

Chemical Formula 7

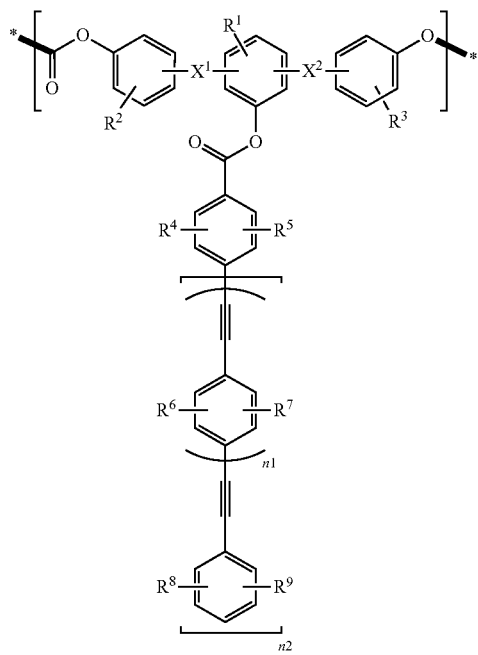

wherein in Chemical Formula 5, $X^1$, $X^2$, and $L^1$ are each independently O, C(=O), C(=O)O, or C(=O)NR$^a$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, n2 is 1 or 2, and

* indicates a binding site to an adjacent atom.

9. The polymer of claim 8, wherein the first structural unit is represented by any one of Chemical Formulae 6 to 8:

-continued

Chemical Formula 8

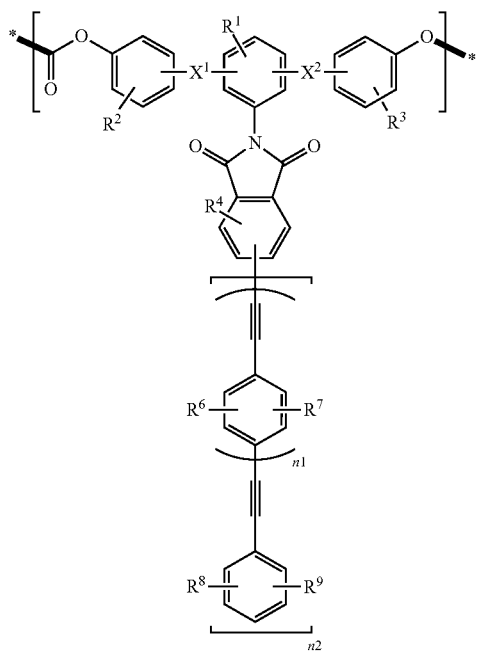

Chemical Formula 6a

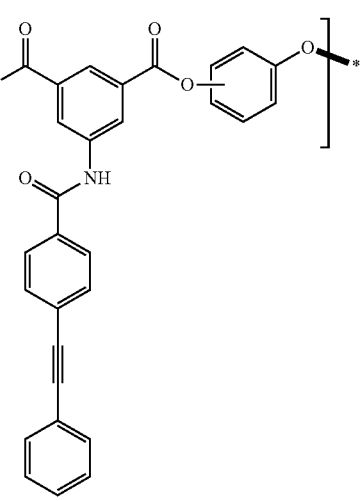

wherein in Chemical Formulae 6 to 8, $X^1$ and $X^2$ are each independently O, C(=O), C(=O)O, or C(=O)NR$^a$, $R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, n1 is an integer ranging from 0 to 3, n2 is 1 or 2, and

* indicates a binding site to an adjacent atom.

10. The polymer of claim 9, wherein the first structural unit represented by Chemical Formula 6 is represented by any one of Chemical Formulae 6a to 6d:

Chemical Formula 6b

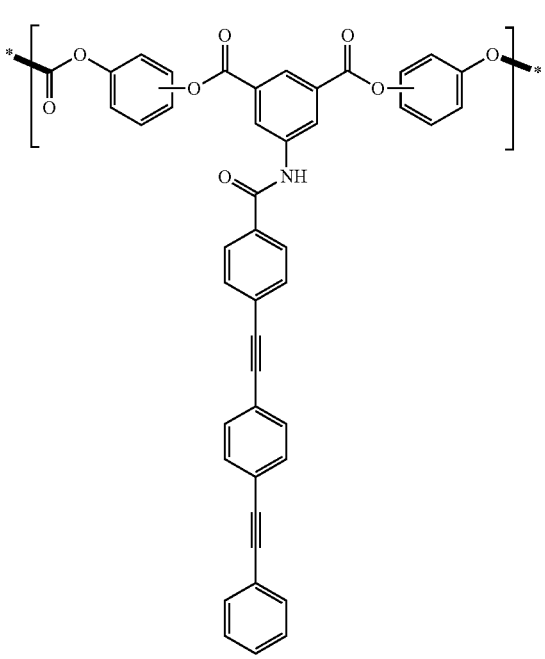

Chemical Formula 6c
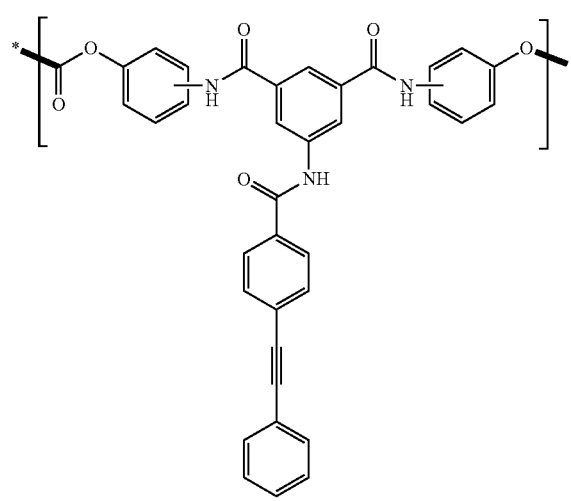
Chemical Formula 7a
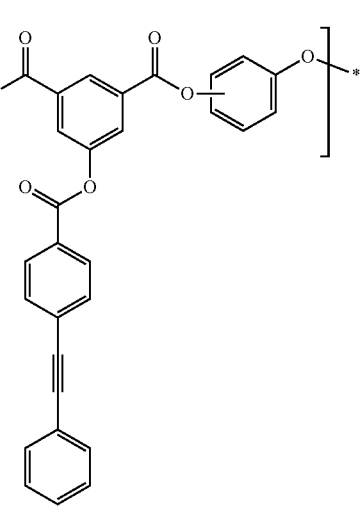
Chemical Formula 6d
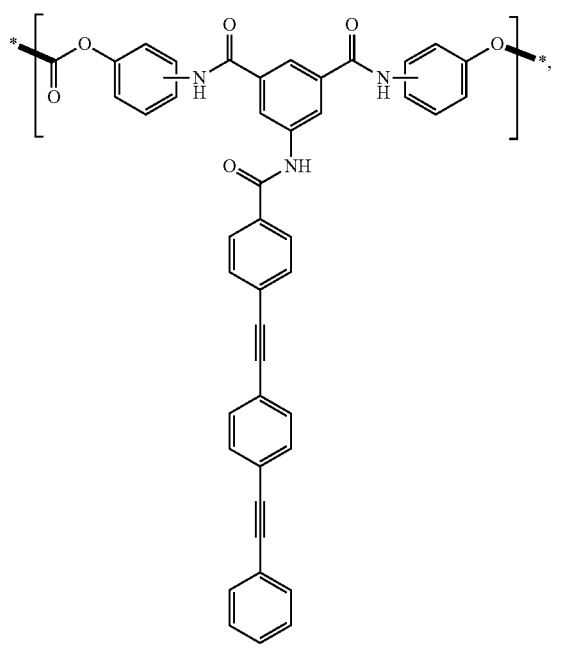
Chemical Formula 7b
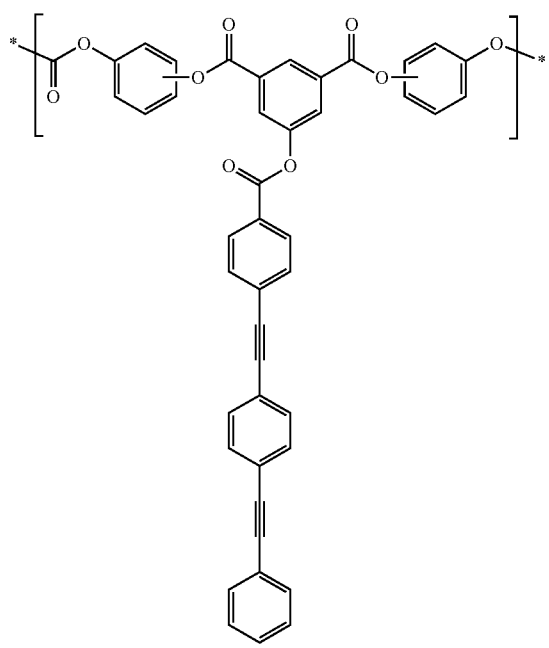
wherein in Chemical Formulae 6a to 6d,
\* indicates a binding site to an adjacent atom.
11. The polymer of claim 9, wherein the first structural unit represented by Chemical Formula 7 is represented by any one of Chemical Formulae 7a to 7d:

Chemical Formula 7c
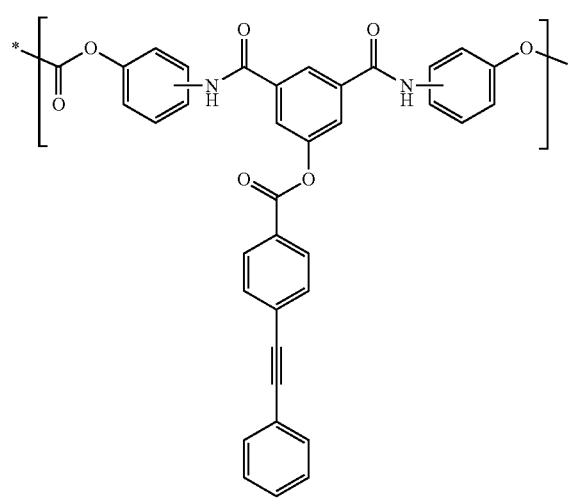
Chemical Formula 8a
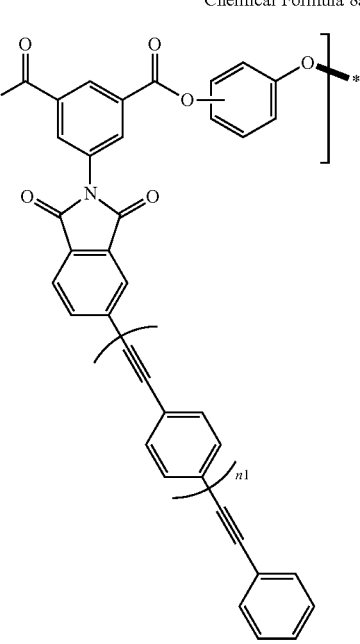
Chemical Formula 7d
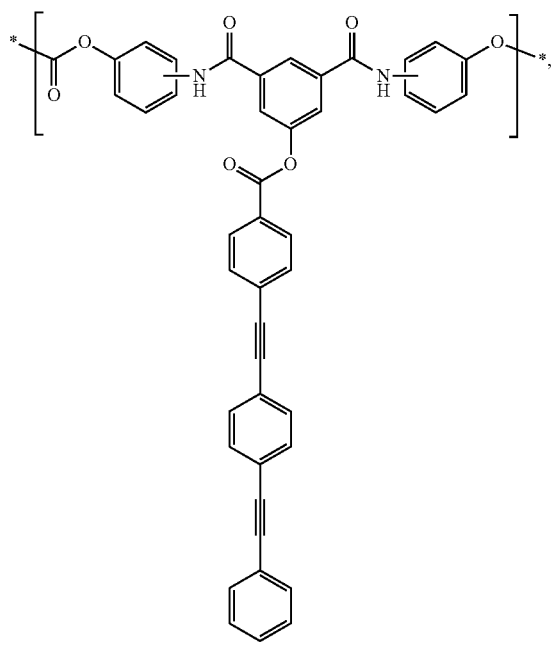
Chemical Formula 8b
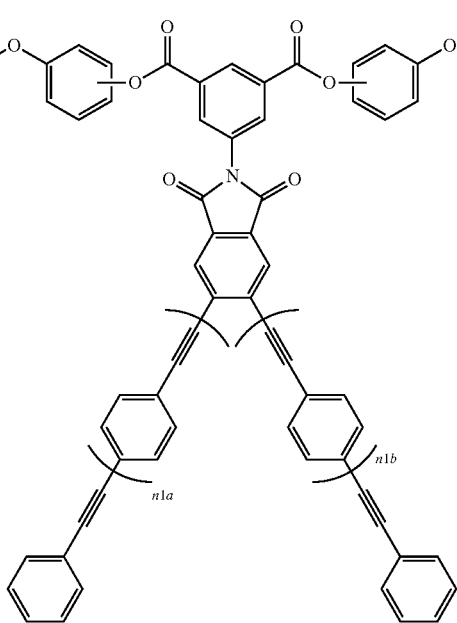
wherein in Chemical Formulae 7a to 7d,
* indicates a binding site to an adjacent atom.
12. The polymer of claim 9, wherein the first structural unit represented by Chemical Formula 8 is represented by any one of Chemical Formulae 8a to 8d:

-continued

Chemical Formula 8c

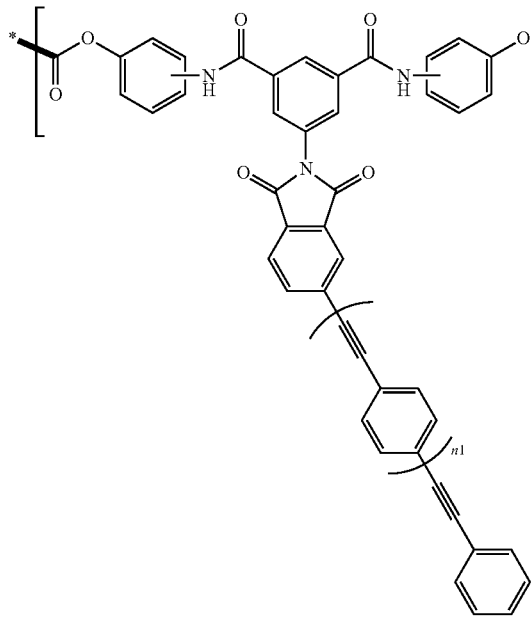

Chemical Formula 9

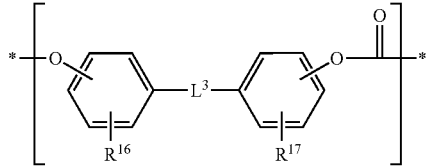

wherein in Chemical Formula 9,
$L^3$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, $R^{16}$ and $R^{17}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

14. The polymer of claim 7, wherein the first structural unit is represented by Chemical Formula 10:

Chemical Formula 10

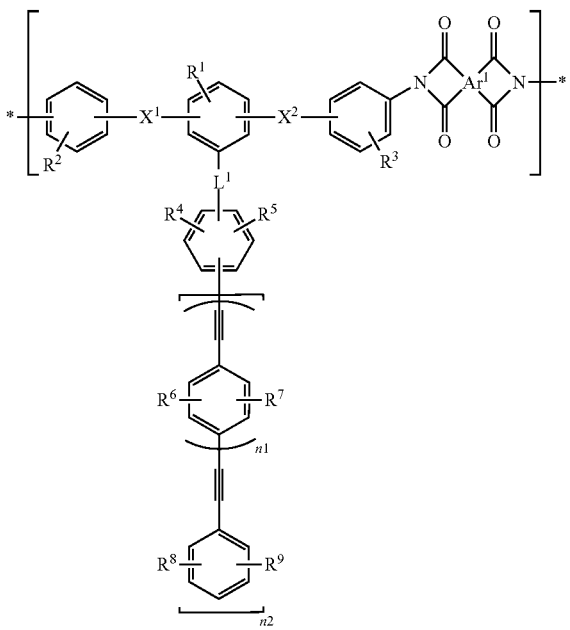

Chemical Formula 8d

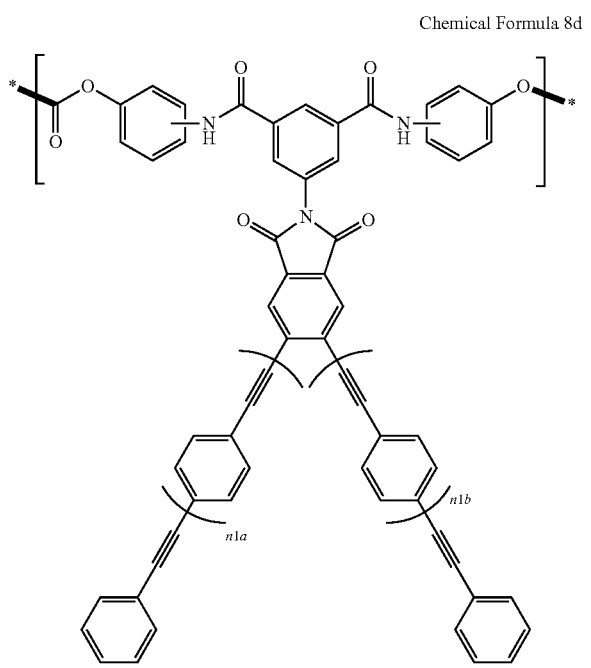

wherein in Chemical Formulae 8a to 8d,
n1, n1a, and n1b are each independently an integer ranging from 0 to 3, and
* indicates a binding site to an adjacent atom.

13. The polymer of claim 8, further comprising a second structural unit represented by Chemical Formula 9:

wherein in Chemical Formula 10,
$X^1$, $X^2$, and $L^1$ are each independently O, C(=O), C(=O)O, or C(=O)$NR^a$,
$Ar^1$ is a substituted or unsubstituted C6 to C30 arylene group,
$R^1$ to $R^9$ and $R^a$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, $L^1$ and $R^5$ are separately present or are linked to provide a ring, n1 is an integer ranging from 0 to 3, n2 is 1 or 2, and

* indicates a binding site to an adjacent atom.

15. The polymer of claim 14, wherein the first structural unit represented by Chemical Formula 10 is represented by any one of Chemical Formulae 11 to 16:

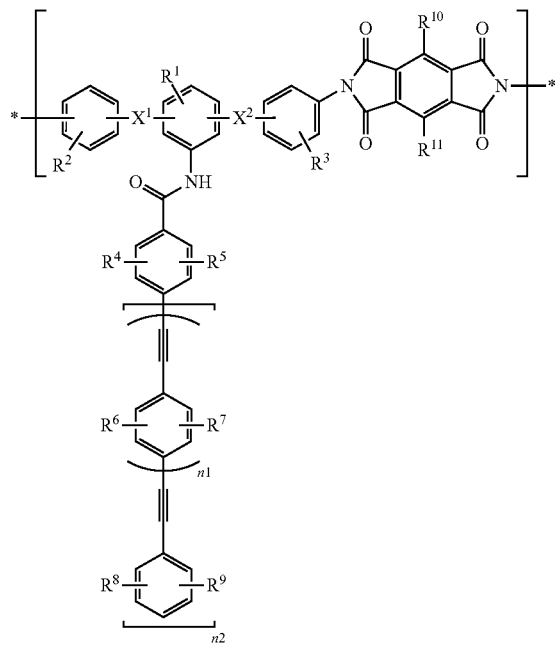

Chemical Formula 11

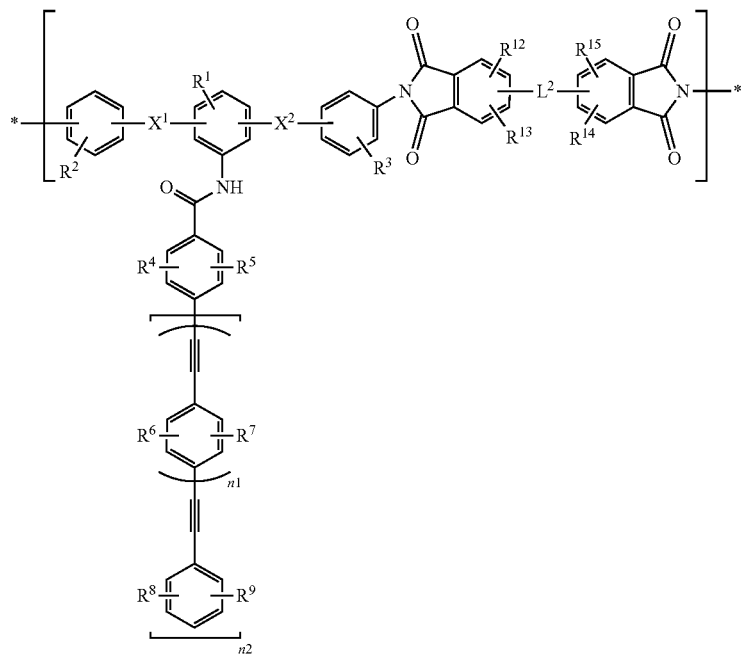

Chemical Formula 12

-continued
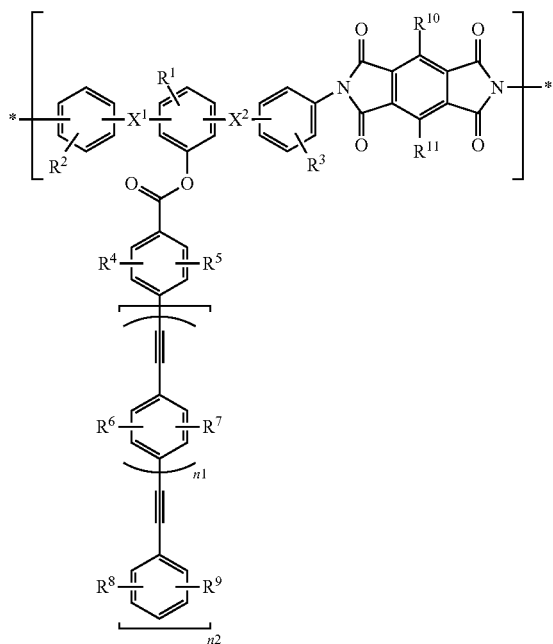
Chemical Formula 13
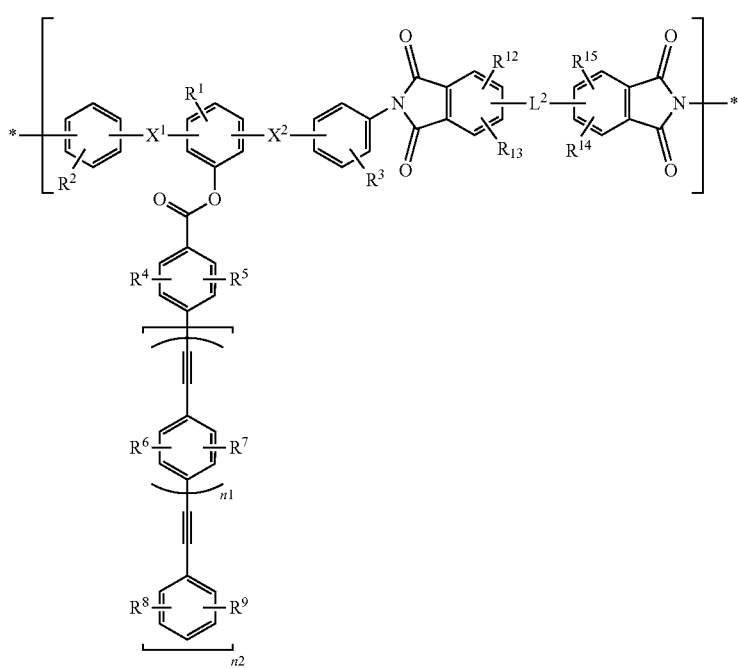
Chemical Formula 14

-continued

Chemical Formula 15

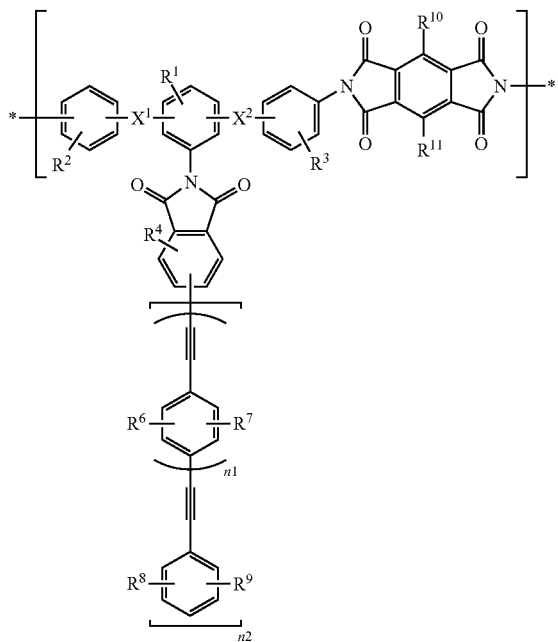

Chemical Formula 16

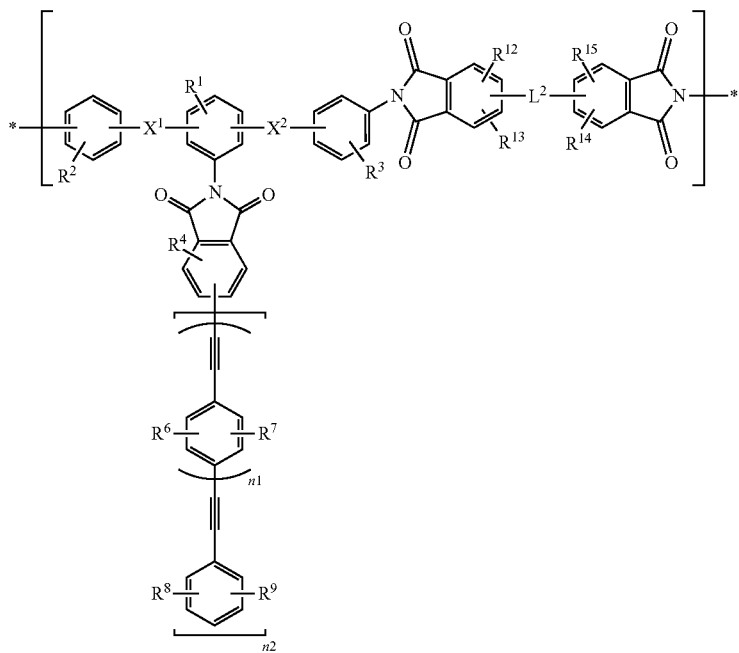

wherein in Chemical Formulae 11 to 16, $X^1$ and $X^2$ are each independently O, CO, COO, or $CONR^a$, $R^1$ to $R^9$ and $R^{12}$ to $R^{15}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a hydrocarbonyl group, a substituted or unsubstituted C2 to C20 alkanoyl group, a substituted or unsubstituted silyl group, a hydroxy group, a halogen, a nitro group, or a combination thereof, n1 is an integer ranging from 0 to 3, n2 is 1 or 2, and

* indicates a binding site to an adjacent atom.

16. The polymer of claim 14, further comprising a second structural unit represented by Chemical Formula 17 or 18:

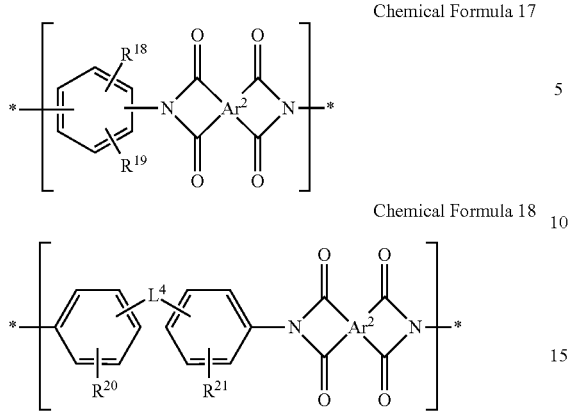

Chemical Formula 17

Chemical Formula 18 wherein in Chemical Formula 17 or 18, $Ar^2$ is a substituted or unsubstituted C6 to C30 arylene group, $L^4$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, CO, COO, $SO_2$, or a combination thereof, $R^{18}$ to $R^{21}$ are each independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and

* indicates a binding site to an adjacent atom.

17. A compensation film comprising the polymer of claim 6.

18. An optical film comprising
the compensation film of claim 17, and
a polarizer.

19. A display device comprising the compensation film of claim 17.

20. A display device comprising the optical film of claim 18.

* * * * *